United States Patent
Ravetch et al.

(10) Patent No.: US 11,690,905 B2
(45) Date of Patent: *Jul. 4, 2023

(54) IMMUNE COMPLEX

(71) Applicant: The Rockefeller University, New York, NY (US)

(72) Inventors: Jeffrey V. Ravetch, New York, NY (US); Taia Wang, New York, NY (US); Jad Mamaary, New York, NY (US)

(73) Assignee: The Rockefeller University, New York, NY (US)

(*) Notice: Subject to any disclaimer, the term of this patent is extended or adjusted under 35 U.S.C. 154(b) by 144 days.

This patent is subject to a terminal disclaimer.

(21) Appl. No.: 17/301,626

(22) Filed: Apr. 9, 2021

(65) Prior Publication Data
US 2021/0228706 A1  Jul. 29, 2021

Related U.S. Application Data

(62) Division of application No. 16/408,517, filed on May 10, 2019, now Pat. No. 10,973,904, which is a division of application No. 15/560,074, filed as application No. PCT/US2016/023426 on Mar. 21, 2016, now Pat. No. 10,300,127.

(60) Provisional application No. 62/136,064, filed on Mar. 20, 2015.

(51) Int. Cl.
| | |
|---|---|
| *A61K 39/00* | (2006.01) |
| *A61K 39/12* | (2006.01) |
| *A61K 39/42* | (2006.01) |
| *C07K 14/005* | (2006.01) |
| *C07K 16/00* | (2006.01) |
| *C07K 16/08* | (2006.01) |
| *C07K 16/12* | (2006.01) |
| *C07K 16/30* | (2006.01) |
| *A61K 39/145* | (2006.01) |
| *C07K 16/10* | (2006.01) |
| *A61P 31/16* | (2006.01) |
| *A61P 35/00* | (2006.01) |
| *A61K 45/06* | (2006.01) |
| *C07K 14/47* | (2006.01) |

(52) U.S. Cl.
CPC ........ *A61K 39/145* (2013.01); *A61K 39/0011* (2013.01); *A61K 39/12* (2013.01); *A61K 39/42* (2013.01); *A61K 45/06* (2013.01); *A61P 31/16* (2018.01); *A61P 35/00* (2018.01); *C07K 14/005* (2013.01); *C07K 14/4748* (2013.01); *C07K 16/1018* (2013.01); *A61K 2039/505* (2013.01); *A61K 2039/5252* (2013.01); *A61K 2039/55516* (2013.01); *C07K 2317/21* (2013.01); *C07K 2317/24* (2013.01); *C07K 2317/31* (2013.01); *C07K 2317/41* (2013.01); *C07K 2317/72* (2013.01); *C07K 2317/76* (2013.01); *C07K 2317/92* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2010/0098719 A1 | 4/2010 | Van Endert et al. | |
| 2011/0076277 A1 | 3/2011 | Ravetch et al. | |
| 2014/0377280 A1 | 12/2014 | Ravetch et al. | |
| 2015/0299331 A1 | 10/2015 | Washburn et al. | |

FOREIGN PATENT DOCUMENTS

WO     2014060712 A1     4/2014

OTHER PUBLICATIONS

GenBank: CAA75032.1. immunoglobulin lambda heavy chain [*Homo sapiens*]. Dated Aug. 19, 1998.*
Anthony et al., "Identification of a receptor required for the anti-inflammatory activity of IVIG," Proceedings of the National Academy of Sciences of the United States of America (Nov. 26, 2008); 105:19571-8.
Choi et al., "A Heterodimeric Fc-Based Bispecific Antibody Simultaneously Targeting VEGFR-2 and Met Exhibits Potent Antitumor Activity," Mol. Cancer Ther (2013) 12(12):2748-59.
Kaneko et al., "Anti-Inflammatory Activity of Immunoglobulin G Resulting from Fc Sialylation," Science (2006); 313:670-673.
Lund et al., "Multiple Interactions of IgG with its Core Oligosaccharide Can Modulate Recognition by Complement and Human Fcγ Receptor I an dINfluence the Synthesis of its Oligosacharide Chains," The Journal of Immunology (1996); 157:4963-4969.
Plincetic et al., "Type I and type II Fc receptors regulate innate and adaptive immunity," Nat Immunol. (Jul. 21, 2014); 15:707-16.
Scallon et al., "Higher levels of sialylated Fc glycans in immunoglobulin G molecules can adversely impact functionality," Molecular Immunology (2007); 44:1524-1534.
Shields et al., "High resolution mapping of the bindig site on human IgG1 for Fc gamma RI, Fc gamma RII, Fc gamma Riii, and FcRn and design of IgG1 variants with improved binding to the Fc gamma R.," J. Biol. Chem. (2001): 276(9):6591-604.
Sondermann et al. "General mechanism for modulating immunoglobulin effector function," Proceedings of the National Academy of Sciences of the United States of America (May 22, 2013); 110:9868-9872.

(Continued)

*Primary Examiner* — Nianxiang Zou
(74) *Attorney, Agent, or Firm* — Fox Rothschild LLP

(57) ABSTRACT

The present invention relates to immunogenic immune complexes, related compositions, and related methods.

21 Claims, 36 Drawing Sheets

Specification includes a Sequence Listing.

(56) References Cited

OTHER PUBLICATIONS

Tharakaraman et al., "Broadly Neutralizing Influenza Hemagglutinin Stem-Specific Antibody CR8020 Targets Residues that Are Prone to Escape due to Host Selection Pressure," Cell Host & Microbe (2014); 15:644-651.

* cited by examiner

FIGURES 1A, 1B and 1C
A
Type I Fc Receptors (IgSF)
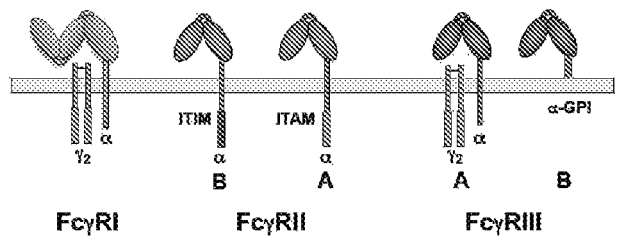
Type II Fc Receptors (C-type lectins)
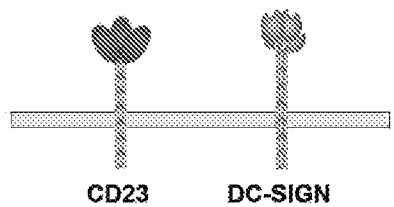
B
IgG subclass distribution
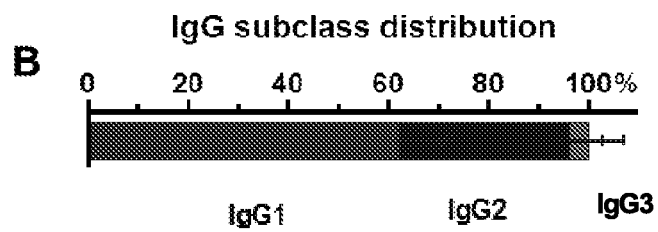
C
Type 1 FcR binding
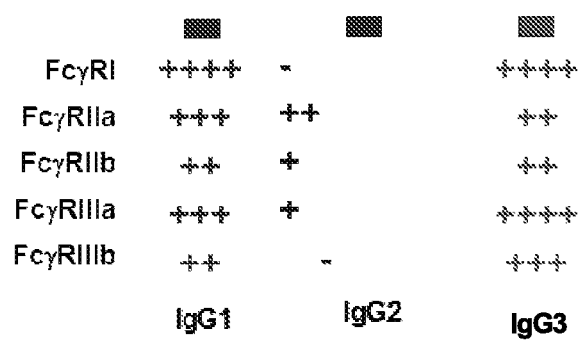

FIGURES 1D, 1E and F
D
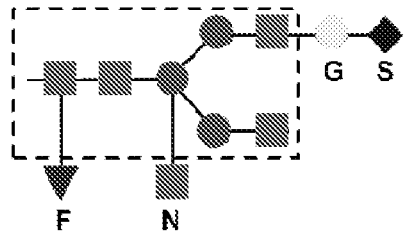
E
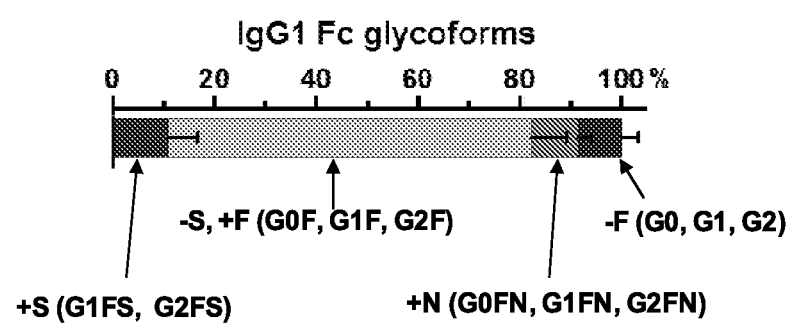
F
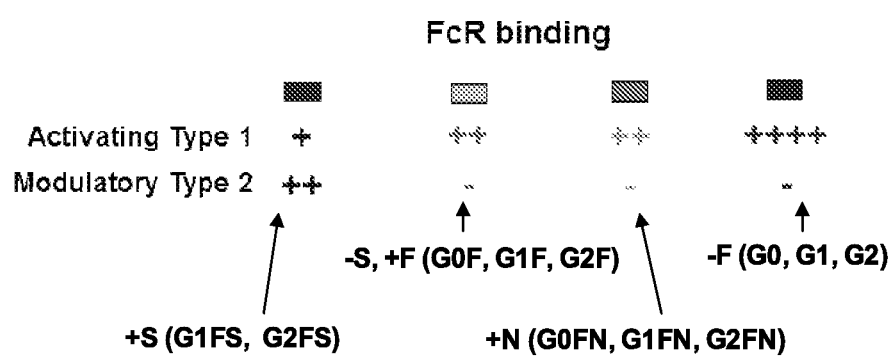

G

H

| Gender (M/F) | 5/5 |
|---|---|
| Age (mean years, range) | 38.6, 23-50 |
| Race | Caucasian: 4<br>African American: 5<br>American Indian: 1<br>Not disclosed: 1 |

A

B

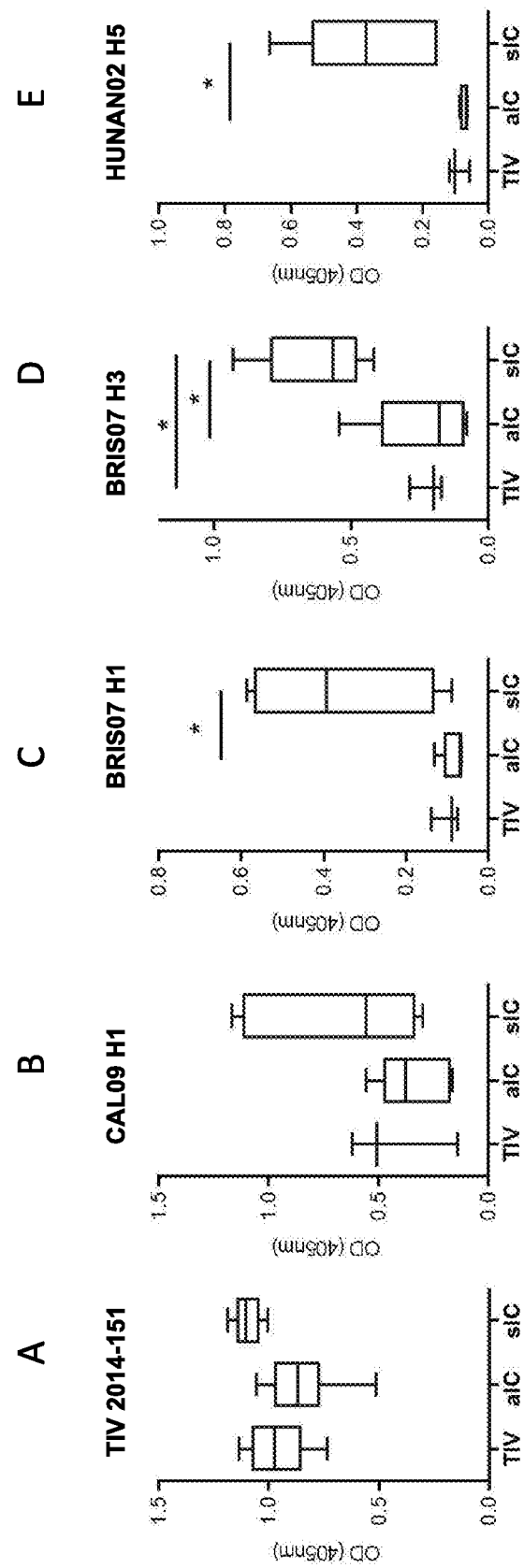
Figures 15A, 15B, 15C, 15D, and 15E

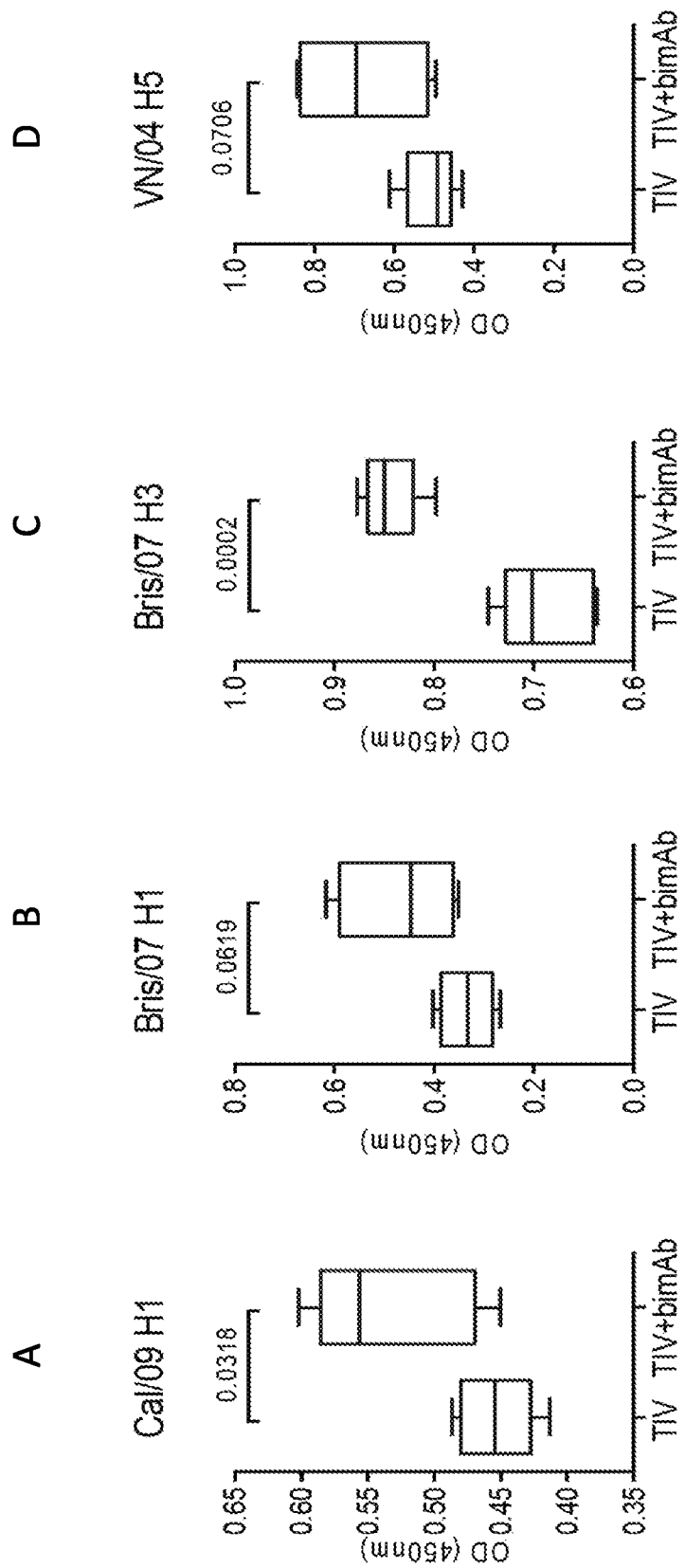
Figures 20A, 20B, 20C, and 20D

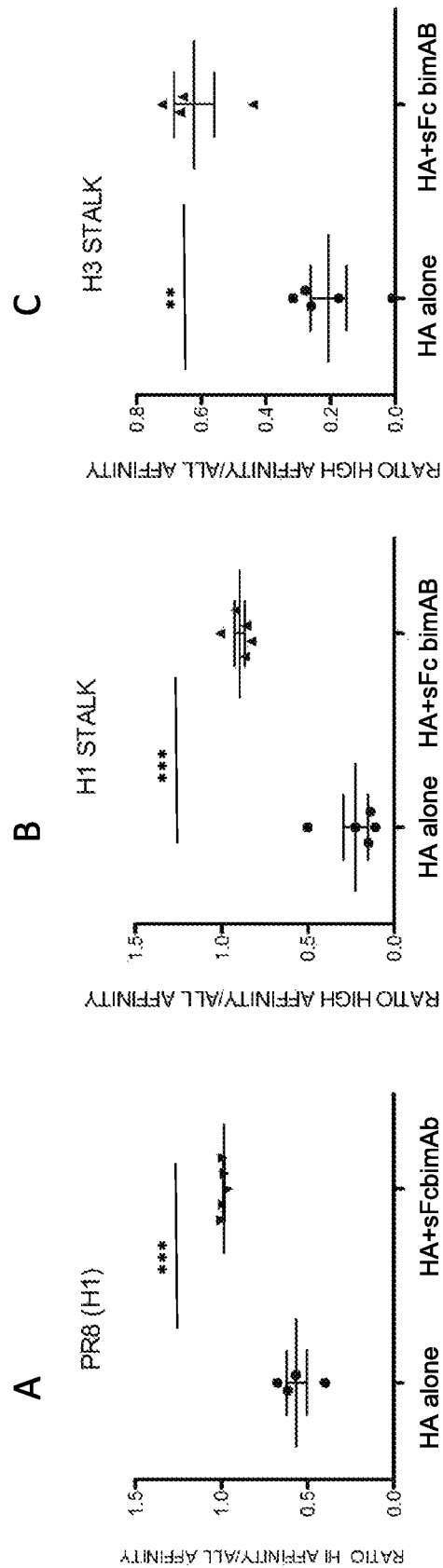
Figures 21A, 21B, and 21C

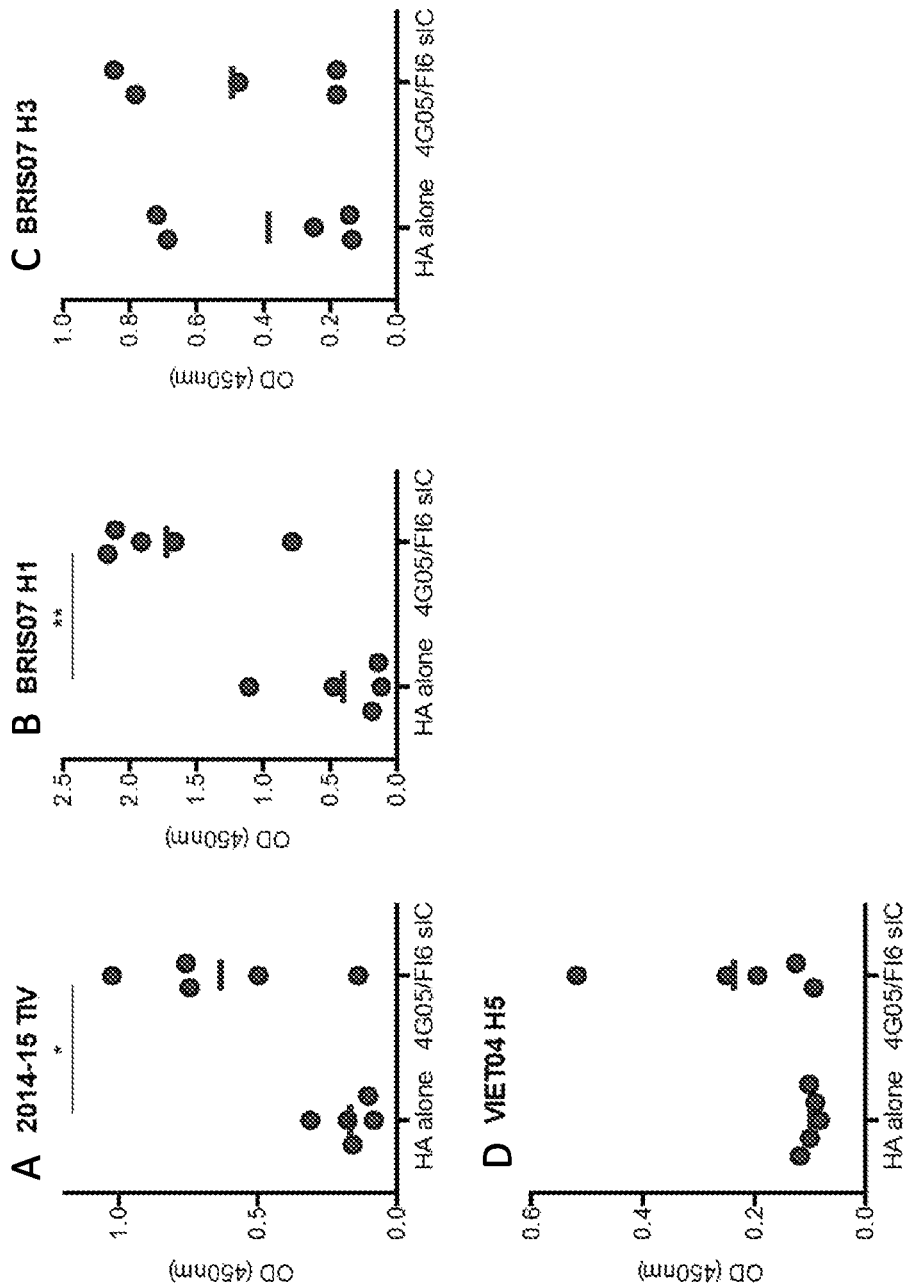
Figures 22A, 22B, 22C, and 22D

SEQUENCE LISTING

```
<160> NUMBER OF SEQ ID NOS: 1

<210> SEQ ID NO 1
<211> LENGTH: 448
<212> TYPE: PRT
<213> ORGANISM: Homo sapiens

<400> SEQUENCE: 1

Cys Glu Val Gln Leu Val Glu Ser Asp Gly Gly Leu Val Gln Pro Gly
1               5                   10                  15

Arg Ser Leu Lys Leu Pro Cys Ala Ala Ser Gly Phe Thr Phe Ser Asp
            20                  25                  30

Tyr Tyr Met Ala Trp Val Arg Gln Ala Pro Thr Lys Gly Leu Glu Trp
        35                  40                  45

Val Ala Ser Ile Ser Tyr Asp Gly Ser Ser Thr Tyr Tyr Arg Asp Ser
    50                  55                  60

Val Lys Gly Arg Phe Thr Ile Ser Arg Asp Asn Ala Lys Ser Thr Leu
65                  70                  75                  80

Tyr Leu Gln Met Asp Ser Leu Arg Ser Glu Asp Thr Ala Thr Tyr Tyr
                85                  90                  95

Cys Gly Arg His Ser Ser Tyr Phe Asp Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

-continued

```
                180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro His
            260                 265                 270
Glu Val Lys Phe Asn Trp Tyr Val Asp Gly Val Glu Val His Asn Ala
            275                 280                 285
Lys Thr Lys Pro Arg Glu Gln Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
```

IMMUNE COMPLEX

CROSS REFERENCE TO RELATED APPLICATION

This application is a Divisional of U.S. patent application Ser. No. 16/408,517, filed May 10, 2019, which is a Divisional of U.S. patent application Ser. No. 15/560,074, filed Sep. 20, 2017, which is the U.S. National Phase of International Patent Application No. PCT/US2016/023426, filed Mar. 21, 2016, which claims priority to U.S. Provisional Application No. 62/136,064 filed on Mar. 20, 2015. The contents of all the applications are incorporated herein by reference in their entirety.

GOVERNMENT INTERESTS

The invention disclosed herein was made, at least in part, with Government support under Grant NOs U19AI111825, U19AI109946, and UL1 TR000043 from the National Institutes of Health. Accordingly, the U.S. Government has certain rights in this invention.

FIELD OF THE INVENTION

This invention relates to immunogenic immune complexes, related compositions, and related methods.

BACKGROUND OF THE INVENTION

The immune system defends the human body against pathogen infection, cellular transformation, and physical/chemical damage. Immunization enables an individual's immune system to become fortified against an agent (known as the immunogen). The basis of immunization, under which vaccination resides, is to generate protective titers of blood-borne antibody as well as memory B-cells that can protect against infectious disease. Typically, vaccines contain agents that resemble a disease causing microorganism and elicit a humoral and/or cellular immune response against the microorganism. These agents can be made of killed microbes, parts of a microbe, or its toxins. All of these immunogens, upon injection, can provide a protective response in a subject. An immunogen, thus, stimulates the body's immune system to recognize exposure to the entire pathogen upon prior exposure to the immunogen itself, and then destroy the pathogen. Generation of a proper vaccine, which is contingent upon finding the proper immunogen that will generate a sufficient protective antibody and memory B-cell response, is a continuing challenge to vaccine development. There remains a continuing unmet need to develop a vaccine which can reliably provide sufficiently immunogenic epitopes and elicit a protective immune response in a subject.

SUMMARY OF INVENTION

This invention addresses the above-described un-met need by providing an immune complex (IC) or immune complexes (ICs), which take advantages of Type II Fc receptor (FcR) interactions and signalling to elicit broader and more potent protective immune responses.

In one aspect, the invention provides an immune complex comprising an antigenic agent and an isolated protein. The protein comprises an IgG Fc region and is capable of binding to a Type II Fc receptor. Preferably, the protein is an antibody or an Fc region-containing fragment thereof. In one embodiment, the protein comprises a sialylated form of an IgG heavy chain (e.g., SEQ ID NO: 1 listed below) or an Fc region-containing fragment thereof. In another embodiment, the protein comprises an asialylated form of the IgG Fc region. In the latter case, the protein can be a FA241 mutant of SEQ ID NO: 1 or the same mutant at the corresponding positions of other IgG Fc region sequences. In the immune complex, the isolated protein specifically binds to the antigenic agent or otherwise conjugated to the antigenic agent to form the immune complex.

In one embodiment, the antigenic agent comprises a polypeptide or other antigenic molecule. For example, the polypeptide can comprise the sequence of an antigen of a virus. Examples of the virus include a picoranovirus, a togovirus, a coronavirus, an arenavirus, a bunyavirus, a rhabdovirus, an orthomyxovirus, a paramyxovirus, a reovirus, a parvovirus, a papovovirus, an adenovirus, a herpesvirus, a varicella-zoster virus, and an RNA tumor virus. Additional examples are described below in the section of detailed description of the invention. Preferably, the virus is selected from the group consisting of an influenza virus, a norovirus, a rotavirus, an Ebola virus, and a HIV. More preferably, the virus is an influenza virus and in that case, the polypeptide can comprise a HA protein of the influenza virus. In another embodiment, the antigenic agent comprises a tumor antigen. Examples of the tumor antigen are described below in the section of detailed description of the invention. In some examples of the immune complexes, the antibody is a bi-specific antibody that binds (i) to two different epitopes of said antigenic agent or (ii) to said antigenic agent and a second antigenic agent respectively.

The invention also provides a pharmaceutical composition comprising an immune complex described above and pharmaceutically acceptable carrier. Examples include an immunogenic or vaccine composition as described below.

The invention further provides a method of preventing a viral infection. The method comprises administering to a subject in need thereof a therapeutically effective amount of an immune complex described above.

The invention further provides a method of preventing an occurrence of a tumor. The method comprises administering to a subject in need thereof the above-described immune complex. Also provided is another method of preventing tumor formation or enhancing survival of a subject having a tumor. The method includes administering to a subject in need thereof an effective amount of the above-described immune complex. This method can further include administering to the subject an effective amount of at least one chemotherapeutic agent selected from the group consisting of 5-fluorouracil, cytarabine, oxaliplatin, paclitaxel and combinations thereof; thereby treating the tumor or enhancing survival of the subject having the tumor. In these methods, the tumor can be selected from the group consisting of colorectal carcinoma; lung carcinoma; breast carcinoma; melanoma; ovarian carcinoma; cervical carcinoma, pancreatic cancer; multiple myeloma; renal cell carcinoma; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL), and chronic lymphocytic leukemia (CLL).

The details of one or more embodiments of the invention are set forth in the description below. Other features, objectives, and advantages of the invention will be apparent from the description and from the claims.

BRIEF DESCRIPTION OF THE DRAWINGS

FIGS. 1A, 1B, 1C, 1D, 1E, and 1F are a set of diagrams showing type I and type II FcR binding characteristics of human IgG subclasses and Fc glycovariants. (A) Overview of type I and type II FcR family (Pincetic et al. (2014) Nature immunology 15, 707-716) (B) Subclass distribution and (C) type I FcR binding characteristics of baseline anti-H1 IgG from a patient cohort (10 healthy adults). IgG4 levels were below the detection limit. (D) Schematic overview of the Fc-associated glycan structure. Composition of the core Fc glycan (boxed) can be modified by addition of fucose (F), N-acetylglucosamine (N), galactose (G) and sialic acid (S) residues. (E) Fc glycoform distribution on baseline anti-H1 IgG from the patient cohort and (F) binding characteristics for type 1 and type 2 FcR (Anthony et al. (2012) Annals of the New York Academy of Sciences 1253, 170-180). Fc glycovariants were categorized into: sialylated (blue; +S (G1FS, G2FS)), afucosylated (red; −F, (G0, G1, G2)) and 'neutral', defined by the presence of fucose and absence of sialic acid (with branching GlcNAc (+N, pink): G0FN,G1FN,G2FN, without branching GlcNAc (−S+F, gray) G0F,G1F,G2F).

FIGS. 15A, 15B, 15C, 15D, and 15E are diagrams showing that polyclonal TIV sIC enhanced breadth of IgG response to different antigens: (A) TIV 2014-15; (B) CAL09 H1; (C) BRIS07 H1; (D) BRIS07 H3; and (E) HUNAN02 H5.

FIGS. 20A, 20B, 20C, and 20D are diagrams showing that immunization with TIV bispecific mAb (bimAb) sICs enhanced breadth of IgG response to different antigens: (A) Cal/09 H1; (B) Bris/07 H1; (C) Bris/07 H3: and (D) VN/04 H5.

FIGS. 21A, 21B, and 21C are diagrams showing that immunization with H1+H3 proteins with sFc bimAb enhanced affinity of IgG response to different antigens: (A) PR8 (H1); (B) H1 Stalk; and (C) H3 Stalk.

FIGS. 22A, 22B, 22C, and 22D are diagrams showing that immunization with H1+H3 proteins with sFc bimAb enhanced breadth of IgG response to different antigens: (A) 2014-15 TIV; (B) Bris07 H1; (C) Bris07 H3: and (D) VN/04 H5.

DETAILED DESCRIPTION OF THE INVENTION

Figure 2A:
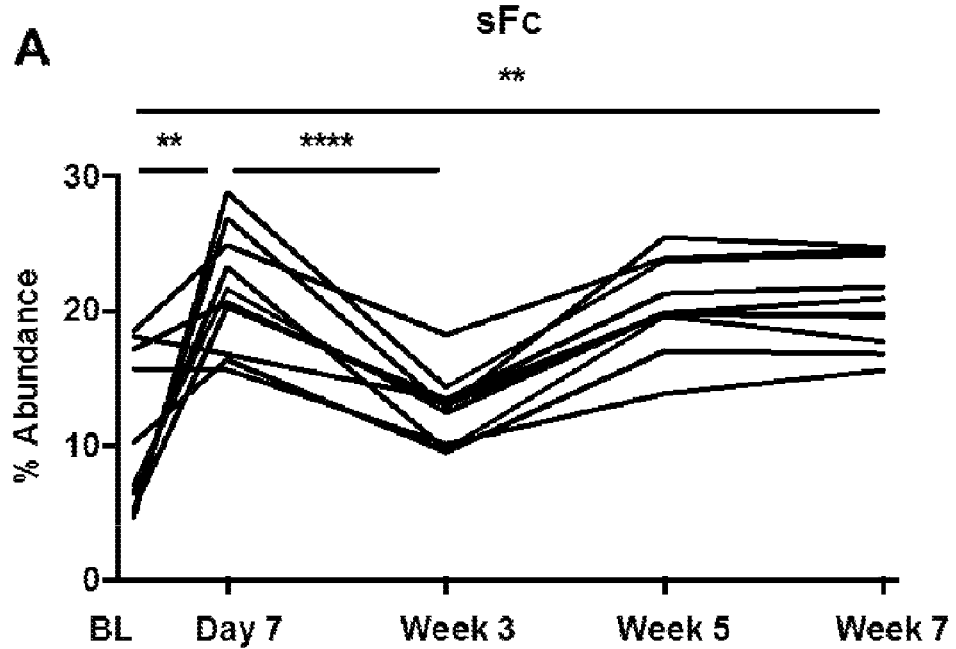
FIGS. 2A, 2B, 2C, 2D, 2E, 2F, and 2G are a set of diagrams showing regulation of Fc glycan composition following Trivalent inactivated influenza vaccine (TIV) vaccination. (A) Sialylated (Type 2 FcR-binding) and (B) fucosylated Fc glycoforms were significantly elevated at day 7 post vaccination, followed by diminution in sialylated and fucosylated glycoforms by week 3. (C) Galactosylation (GalFc) levels were modulated to a small, but statistically significant degree following vaccination. (D) Bisected GlcNAc (bGlcNAcFc) modifications were not regulated. (E,F) Anti-HA IgG (predominantly globular head-specific) and anti-HA stalk IgG differed significantly in Fc glycoform profile at week 3 post vaccination, with sialylated, fucosylated glycan levels highest on globular head-specific IgGs and lowest on stalk-specific IgG. (G) No difference was observed in level of bisecting GlcNAc between total HA and stalk-specific IgG. $*p<0.05$; $p<0.01$; $*p<0.001$; $****p<0.0001$ determined by two-tailed, paired students t tests.
Figure 2B:
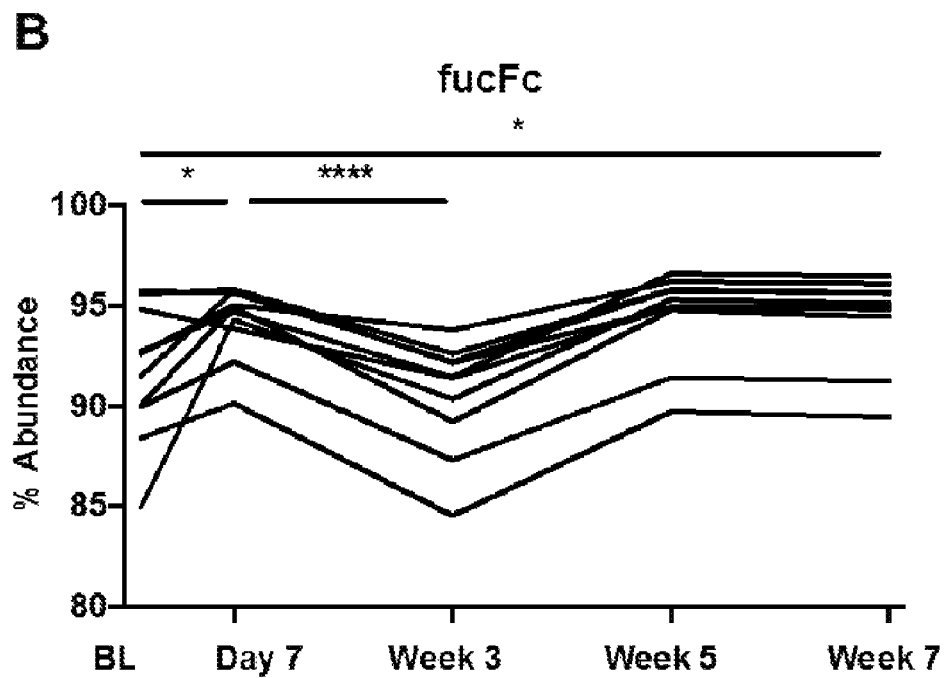

This invention is based, at least in part, on an unexpected discovery and inventive use of a novel, endogenous pathway for affinity maturation. This pathway can be used for eliciting high affinity, broadly neutralizing antibodies through immunization with sialylated immune complexes (ICs).

As disclosed herein, protective vaccines elicit high affinity, neutralizing antibodies by selection of somatically hypermutated B-cell antigen receptors (BCR) on ICs. This implicates Fc-Fc receptor (FcR) interactions in affinity maturation, which, in turn, are determined by IgG subclass and Fc glycan composition within ICs. As disclosed in the examples below, trivalent influenza virus vaccination elicited regulation of anti-hemagglutinin (HA) IgG subclass and Fc glycans, with abundance of sialylated Fc glycans (sFc) predicting quality of vaccine response. It was shown that sFc drive BCR affinity selection by binding the Type-II FcR CD23, thus upregulating the inhibitory FcγRIIB on activated B-cells. This elevates the threshold requirement for BCR signaling, resulting in B-cell selection producing higher affinity IgG. As a result, immunization with sFc HA ICs elicited protective, high affinity IgGs against the conserved stalk of the HA.

IC-FcR Interactions and Fc Sialylation

IC-FcR interactions mediate a wide array of cellular processes required for maturation of protective, vaccine-induced antibody responses including efficient transport of antigen to the germinal center, activation of T follicular helper cells and selection of high affinity B cells. Indeed, FcR signaling is responsible, in large part, for maintaining the balanced positive and negative signaling that culminates in appropriate immune responses (Pincetic et al. (2014) Nature immunology 15, 707-716). Two basic classes of FcRs have been identified: Type I FcRs are immunoglobulin superfamily members and include FcγRI, II, and III, while Type II FcRs are C-type lectin family members and include DC-SIGN and CD23 (FIG. 1a). Perturbations in either signaling arm result in changes in antibody affinity and peripheral tolerance (Bolland et al. (2000) Immunity 13, 277-285). IC-FcR interactions can initiate activating, inhibitory or modulatory cell signaling depending on the pattern of FcRs engaged, which is determined by the structure of Fc domains within an IC. Fc structure, in turn, is regulated by IgG subclass and Fc glycan composition.

IgG antibodies exist as four subclasses in humans (IgG1-4) with IgG1 in highest abundance in serum followed by IgG2>IgG3>IgG4. This was demonstrated by the subclass distribution of baseline (pre-vaccination) anti-HA IgGs from a cohort of 10 healthy adult volunteers described in the examples below (FIG. 1b, FIG. 8). Each subclass is distinct in its ratio of binding to activating:inhibitory Type 1 FcγRs, with IgG1 and IgG3 having the highest activating receptor binding affinities (FIG. 1c) (Morell et al. (1970) The Journal of clinical investigation 49, 673-680).

The Fc glycan is an N-linked, complex, biantennary glycan that is attached within the Cγ2 domain at Asn-297 of each IgG heavy chain and its presence is essential for all Fc-FcR binding interactions (Anthony et al. (2010) Journal of clinical immunology 30 Suppl 1, S9-14). Composition of the core Fc glycan heptasaccharide can be modified by addition of specific saccharide units (fucose (F), N-acetylglucosamine (N), galactose (G) and sialic acid (S)) (Figure id); these modifications are dynamic and act to regulate the biological activity of IgG molecules by modulating Fc structure and, as a consequence, IC-FcR interactions. At baseline, a majority of IgG Fc glycoforms are of "neutral" composition, defined by the presence of fucose (fucFc) and absence of sialic acid. sFc is present with an abundance of ~5-20% and afucosylated Fc (afucFc) glycoforms are found with an abundance of ~5-15%. This distribution was demonstrated by the baseline Fc glycoform composition on anti-HA IgG1 of the patient cohort (FIG. 1e). The most biologically significant modifications to Fc glycan composition are sialylation and fucosylation: the presence of both sialic acid and fucose is inhibitory for Type I Fc receptor binding, while the absence of fucose enhances binding to the activating Type 1 FcγRIIIa. The presence of sialic acid alone is the determinant of Type II FcR binding (FIG. 1f) (Anthony et al. (2008a) Science 320, 373-376; and Sondermann et al. (2013) Proceedings of the National Academy of Sciences of the United States of America 110, 9868-9872). Sialylation has the effect of increasing the conformational flexibility of the Cγ2 domain, enabling the Fc to sample a more "closed" conformation (Ahmed et al. (2014) Journal of molecular biology 426, 3166-3179), thereby exposing binding sites for Type II FcRs with correspondingly reduced Type 1 FcR binding potential. Sialylation of the Fc glycan therefore represents a mechanism for regulating the effector activity of immunoglobulins through alternation of Fc conformations between open and closed states, thus regulating Fc binding to Type I or Type II FcRs, respectively (Sondermann et al. (2013) Proceedings of the National Academy of Sciences of the United States of America 110, 9868-9872).

Studies on the bisecting GlcNAc modification show possible increased Type I FcγRIIIa binding affinity, however afucosylation is a far more potent determinant of strong FcγRIIIa binding (Hodoniczky et al. (2005) Biotechnology progress 21, 1644-1652; Shields et al. (2002) The Journal of biological chemistry 277, 26733-26740; Shinkawa et al. (2003) The Journal of biological chemistry 278, 3466-3473; and Umana et al. (1999) Nature biotechnology 17, 176-180). Addition of galactose alone to one or both arms of the branched Fc glycan does not affect FcR binding, but is significant because galactosylation is a prerequisite for sialylation.

Shifting IgG Fc binding specificity from Type I to Type II FcRs can result in significant in vivo responses and precise regulation of sFc abundance is likely a fundamental homeostatic process. One known consequence of increasing Type II FcR signaling is anti-inflammatory activity, a classic example of which is the therapeutic anti-inflammatory activity of high dose intravenous immunoglobulin (IVIG) (Anthony et al. (2008a) Science 320, 373-376; Kaneko et al. (2006) Science 313, 670-673; and Washburn et al. (2015) Proceedings of the National Academy of Sciences of the United States of America). sFc in IVIG, acting through binding of the Type II FcR DC-SIGN on innate effector cells, stimulates IL-33 production resulting in downstream anti-inflammatory processes (Anthony et al. (2011) Nature 475, 110-113). Disrupted balance in Type I and Type II FcR signaling likely occurs in several inflammatory diseases such as rheumatoid arthritis and granulomatosis with polyangiitis in which decreased abundance of sFc are found on autoantibodies such as anti-citrullinated peptide (ACPA) and anti-proteinase 3 (PR3) antibodies, respectively. Sialylation of anti-ACPA and anti-PR3 Fcs is reduced during disease flares, while disease remission is correlated with elevated Fc glycan sialylation of those autoantibodies (de Man et al. (2014) Current opinion in rheumatology 26, 329-333; Espy et al. (2011a) Arthritis & Rheumatism 63, 2105-2115; Scherer et al. (2010) Arthritis and rheumatism 62, 1620-1629; Tomana et al. (1988) Arthritis and rheumatism 31, 333-338; and van de Geijn et al. (2009) Arthritis research & therapy 11, R193).

Just as sialic acid-modified Fc glycans play a critical role in the regulation of inflammatory processes, the presence or absence of a branching fucose moiety modulates the interaction of IgG Fcs with FcγRIIIa to enhance or inhibit IgG-mediated ADCC and monocyte/macrophage activation (Okazaki et al. (2004) Journal of molecular biology 336, 1239-1249; Shields et al. (2002) The Journal of biological chemistry 277, 26733-26740; Umana et al. (1999) Nature biotechnology 17, 176-180; and Shinkawa et al. (2003) The Journal of biological chemistry 278, 3466-3473). Afucosylated Fc domains have increased affinity for the activating receptor FcγRIIIa that results from a stabilizing interaction between the N-glycan on FcγRIIIa with the afucosylated Fc glycan (Ferrara et al. (2011) Proceedings of the National Academy of Sciences of the United States of America 108, 12669-12674). Removal of fucose from monoclonal therapeutic antibodies such as rituximab and trastuzumab improved their clinical efficacy by increasing binding to FcγRIIIa, thereby enhancing ADCC activity (Dalle et al. (2011) Molecular cancer therapeutics 10, 178-185 and Junttila et al. (2010) Cancer research 70, 4481-4489). As with sialylated glycoforms, diseases associated with modulations in fucose levels on Fc glycans suggests strict regulation of Fc fucosylation; for example, in fetal or neonatal alloimmune thrombocytopenia, IgG specific for human platelet antigens (HPA) have significantly diminished levels of fucosylated Fc glycans, with levels of afucosylated anti-HPA correlating with disease severity (Kapur et al. (2014) Blood 123, 471-480).

That Fc glycan modulation may result in autocrine B cell signaling through IC-FcR interactions, potentially directing the antibody response to vaccination, is suggested by the observations that Fc glycan composition can change following vaccination (Selman et al. (2012) Molecular & cellular proteomics: MCP 11, M111 014563) and that sFc can bind CD23, the Type II FcR expressed on activated B cells (Sondermann et al. (2013) Proceedings of the National Academy of Sciences of the United States of America 110, 9868-9872).

As shown in the examples below, a study was designed to determine whether Fc structure within vaccine antigen-IgG ICs might be regulated as a mechanism of directing FcR-mediated processes involved in maturation of antibody responses. The approach was to characterize modulations in IgG subclass and Fc glycan composition on IgGs elicited by administration of trivalent influenza virus vaccine (TIV) in healthy subjects. Next, a series of directed experiments were performed to determine what role the modulations played in determining vaccine responses. The results on the natural regulation of Fc domain structure during the evolution of protective vaccine responses suggest immunization strategies involving administration of ICs containing sFc to elicit broadly protective antibodies against influenza viruses.

Figure 13:
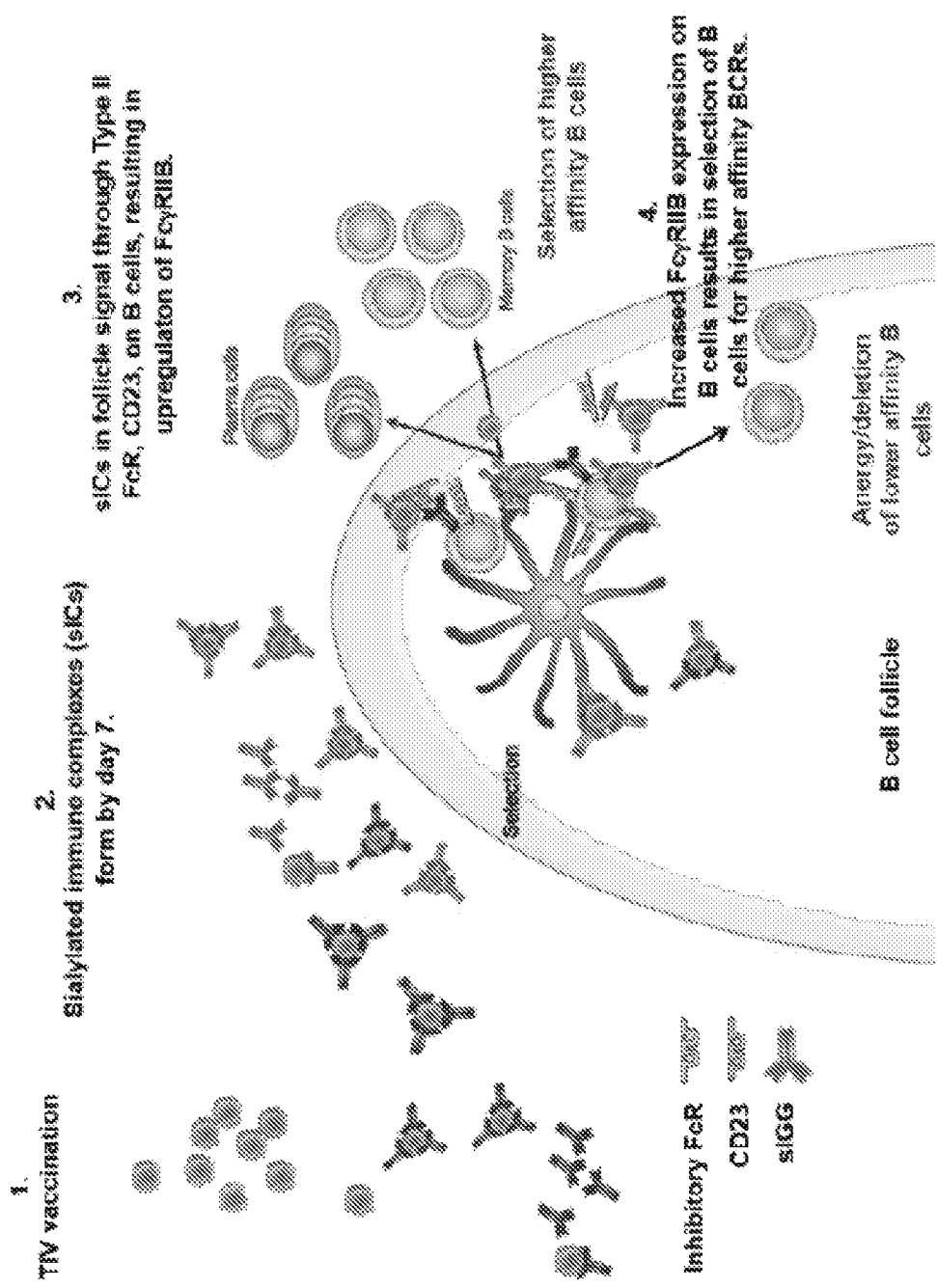
FIG. 13 shows a model whereby sialylated ICs increase selective pressure on B cells by triggering increased FcγRIIb expression through CD23; this results in increased threshold of BCR affinity required for cell survival and selection of B cells with higher affinity for antigen, thus elevating the affinity of antibody elicited during vaccination.

For example, that sFc produced during the early plasmablast response was found to correlate with subsequent production of neutralizing antibody suggested a possible requirement for immunomodulatory Type 2 FcR signaling in the ontogeny of protective TIV responses. Further experiments demonstrated that, sFc within immune complexes triggered upregulation of B cell FcγRIIb, thus modulating the selection of B cells in favor of those expressing higher affinity BCR. The studies disclosed herein suggest a model whereby TIV vaccination triggers plasmablast expansion with associated elevation in abundance of sFc IgG. This IgG forms complexes with the HA vaccine antigen and, through IC-Type II FcR signaling (CD23) on B cells, FcγRIIb expression is upregulated. This results in increased threshold of BCR affinity required for cell survival and production of higher affinity IgG, thus elevating the quality of antibody elicited during vaccination (FIG. 13).

Figures 14A, 14B, 14C:
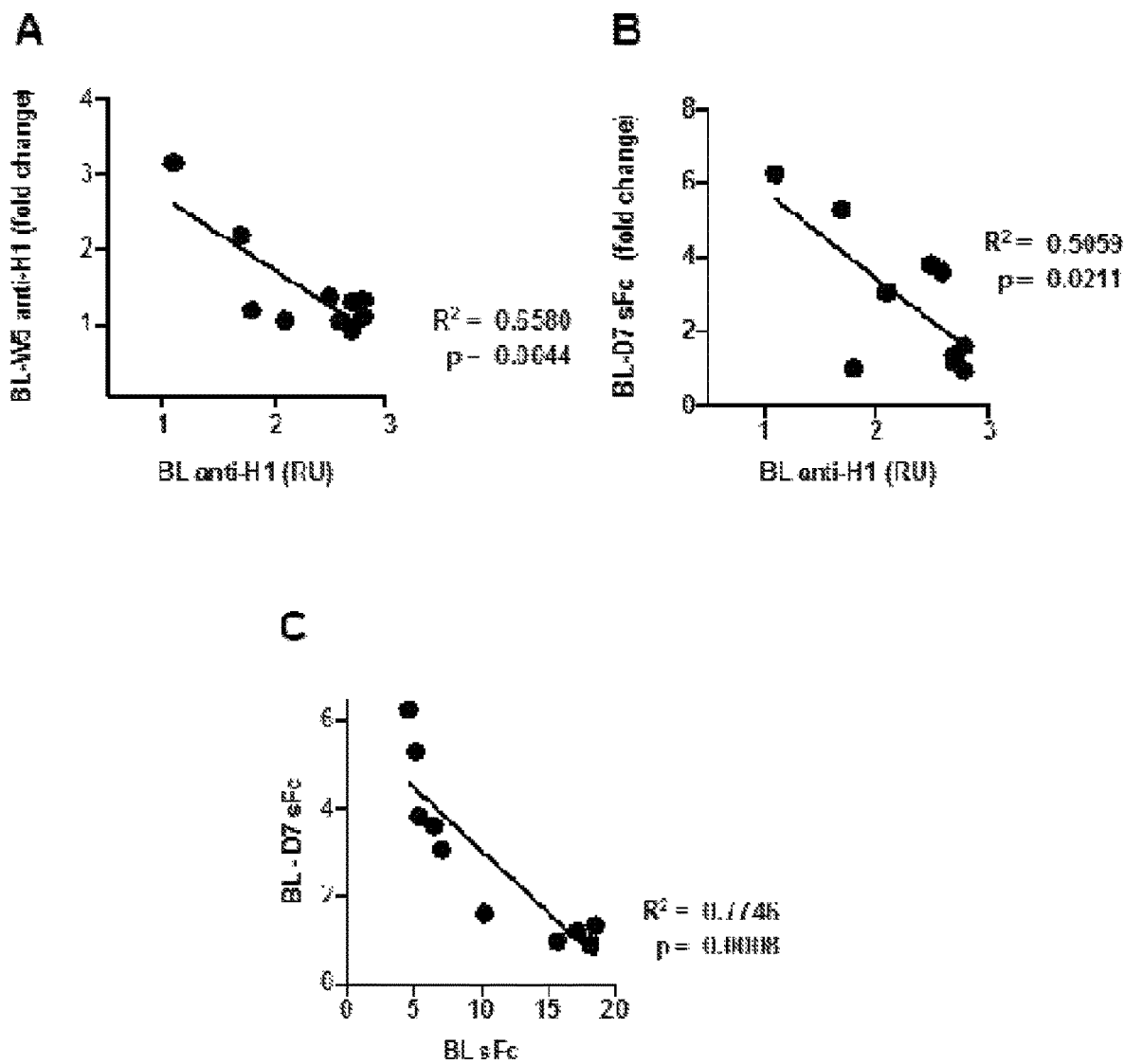
FIGS. 14A, 14B, and 14C are diagrams showing correlations between baseline anti-HA IgG and subsequent antibody response. (A) The magnitude of anti-H1 IgG present at baseline correlated negatively with the anti-H1 vaccine response and (B) abundance of sialylated glycoforms produced in the week following vaccination. (C) Baseline sialylated Fc glycan abundance on anti-H1 IgG correlated negatively with the abundance of sialylated glycoforms produced in the week following vaccination. Correlation analysis was used to determine the Pearson correlation coefficient, r. Linear regression was used to determine goodness of fit, $R^2$.

Several studies, including the studies disclosed herein, have found that baseline titer of anti-HA IgG correlates negatively with the magnitude of TIV response, so that low baseline titer predicts greater vaccine response (FIG. 14a) (Beyer et al. (1996) Vaccine 14, 1331-1339; He et al. (2008) PloS one 3, e2574; Sasaki et al. (2008) PloS one 3, e2975; and Tsang et al. (2014) Cell 157, 499-513). Low baseline anti-HA titer also predicts greater plasmablast frequency (Tsang et al. (2014) Cell 157, 499-513) and greater production of sialylated Fc glycoforms by day 7 post vaccination (FIG. 14b). Overall, low baseline anti-HA IgG predicts large plasmablast expansion and abundant production of sialylated glycoforms within the week following vaccination, resulting in protective TIV vaccine response. Of note, greater production of sialylated Fc glycoforms by day 7 could also be predicted by baseline sialylated Fc abundance, with lower baseline sialylated glycoform abundance preceding greater subsequent production (FIG. 14c).

The finding that protective anti-stalk IgGs can be elicited by sialylated ICs is significant as anti-stalk IgGs can mediate broad protection against antigenically distinct influenza viruses (Henry Dunand et al. (2015) The Journal of clinical investigation 125, 1255-1268; Krammer et al. (2015) Nature reviews Drug discovery 14, 167-182; Krammer et al. (2013) Journal of virology 87, 6542-6550; Pica et al. (2012) Proceedings of the National Academy of Sciences of the United States of America 109, 2573-2578; and Wang et al. (2010) PLoS pathogens 6, e1000796). In view of the observation that sialylated immune complexes can drive selection of higher affinity B cells, one can use this as a strategy to selectively elicit higher affinity anti-stalk IgGs, thereby generating broader and more potent anti-HA responses. The finding also suggests an affinity requirement for protective anti-stalk IgGs that is not present for globular head-specific antibodies; it is possible that higher affinity may be required of anti-stalk IgGs in order to restrict the conformation change in the HA that occurs at low pH, thus preventing fusion of the viral envelope with the host cell.

Because balanced FcR signaling is a requirement for generation of specific immune responses, strict regulation of Fc domain structure within ICs must occur (Fukuyama et al. (2005) Nature immunology 6, 99-106). As disclosed herein, this regulation occurs through synchronized modulations in determinants of Fc domain structure following exposure to antigen. The changes observed, over the weeks following vaccination, would regulate Type 1 and Type 2 FcR signaling within B cell follicles where antigen can be retained for months and even years following exposure (Nossal (1992) Cell 68, 1-2). Plasmablasts that expand following TIV are a likely source of sFc IgG observed at day 7, while memory B cells may contribute to production of the less fucosylated, less sialylated Fc glycoforms observed at week 3. Production of less fucosylated, less sialylated glycoforms by memory B cells may be supported by the finding that these glycoforms are present with greater abundance on IgGs specific for the highly conserved stalk domain of the HA. A shift toward Fc domains with increased Type I FcR binding at week 3 was pronounced in both Fc glyco form and IgG subclass distribution. A possible function of increased activating Type I FcR signaling at week 3 may be to provide an adaptive mechanism for enhancing phagocyte activity during prolonged antigen exposure or infection.

Immune Complexes

As disclosed herein, immune complexes contains two components, an antigen and a sialylated antibody or its Fc-containing, function variant, and can elicit high affinity, broadly neutralizing antibodies. Accordingly, one aspect of this invention provides such immune complexes, which can be used as vaccine capable of eliciting a protective prophylactic immune response and/or a therapeutic immune response in vivo.

As used herein, an immune complex or IC comprises an antigen of interest and an antibody or its Fc region-containing variant. The complex can be formed via conventional antibody-antigen binding between an antibody (or its variant) and an antigen to which the antibody is bound. Alternatively, the complex can be formed via other means, such as chemical conjugation or recombinant technology, e.g., a fusion protein. In other words, in the latter case, the complex is not necessarily formed via conventional antibody-antigen binding. Instead, the immune complex can be formed through means such chemical bonds or peptide bonds (e.g., in a fusion protein of IgG Fc and the antigen). The immune complex here does not include naturally occurring antigen-antibody complexes. Either or both of the above-mentioned two components are man-made, e.g., by recombinant DNA technology, and the complexes can be formed in vitro. For example, either or both can have one or more mutation or sequence heterologous to the naturally occurring counterparts. In some example, either can be artificially modified (e.g., pegylation and sialylation) to improve certain property of the complex, e.g., stability and binding to a receptor (such as Type II FcR). Examples of the antibody may include, by way of example, monoclonal and polyclonal antibodies; chimeric and humanized antibodies; human and non-human antibodies; wholly synthetic antibodies; and single chain antibodies.

2A. Antibody/Fc-Containing Component

The skilled artisan will understand that there are no limitations on the identities of the antibodies in the immune complexes of the present invention. For example, the antibodies or variants thereof may be obtained from any species of animal, though preferably from a mammal such as a human, simian, mouse, rat, rabbit, guinea pig, horse, cow, sheep, goat, pig, dog or cat. Preferably the antibodies are human antibodies. Preferably, the antibody is a class of IgGs or IgEs, including IgG1, IgG2, IgG3, and IgG4. Antibody fragments of less than the entire antibody may be used, with the only limitation being that the antibody fragments retain the ability to bind to a Type II FcR, such as C-type lectin family members including DC-SIGN and CD23 (FIG. 1a). Shown below is an exemplary human IgG1 heavy chain sequence, where the Asn297 (N297) and Phe241 (F241) resides are underlined.

```
                                              (SEQ ID NO: 1)
CEVQLVESDGGLVQPGRSLKLPCAASGFTFSDYYMAWVRQAPTKGLEW

VASISYDGSSTYYRDSVKGRFTISRDNAKSTLYLQMDSLRSEDTATYY

CGRHSSYFDYWGQGVMVTVSSASTKGPSVFPLAPSSKSTSGGTAALGC

LVKDYFPEPVTVSWNSGALTSGVHTFPAVLQSSGLYSLSSWTVPSSSL

GTQTYICNVNHKPSNTKVDKRVEPKSCDKTHTCPPCPAPELLGGPSVF

LFPPKPKDTLMISRTPEVTCVVVDVSHEDPHEVKFNWYVDGVEVHNAK

TKPREQQYNSTYRVVSVLTVLHQDWLNGKEYKCKVSNKALPAPIEKTI

SKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEAL

HNHYTQKSLSLSPGK
```

Examples of Fc-containing protein can be used in the immune complex disclosed herein include SEQ ID NO: 1, Fc-containing fragments therefore (e.g., regions containing K210-K448, C226-K448, or P230-K448 of SEQ ID NO: 1), and their functional variants. K210, C226, P230, and K448 are underlined. A functional variant of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the activity to of the ability to bind to a Type II FcR, such as C-type lectin family members including DC-SIGN and CD23 and to trigger the respective cellular response. The isolated polypeptide can contain SEQ ID NO: 1 or an Fc-containing fragment (e.g., regions containing K210-K448, C226-K448, or P230-K448 of SEQ ID NO: 1) or variant thereof. In general, the functional equivalent is at least 70% (e.g., any number between 70% and 100%, inclusive, e.g., 70%, 80%, 85%, 90%, 95%, and 99%) identical to SEQ ID NO: 1 or an Fc-containing fragment (e.g., regions containing K210-K448, C226-K448, or P230-K448 of SEQ ID NO: 1).

The amino acid composition of the above-mentioned antibody or variant thereof may vary without disrupting the ability to bind to Type II FcR and trigger the related cellular response. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 can be replaced with another amino acid residue from the same side chain family. Alternatively, mutations can be introduced randomly along all or part of the sequences, such as by saturation mutagenesis, and the resultant mutants can be screened for the ability to bind to the respective receptor and trigger the respective cellular response to identify mutants that retain the activity as described in, e.g., WO2013/095973 and US20140377280, the contents of which are incorporated by reference in their entireties.

As disclosed herein the Fc-containing component of the immune complex should be either sialylated at Asn-297, or non-sialylated but assume a conformation similar to the sialylated form and can bind to Type II FcRs. It is known that certain non-sialylated IgG Fc variants bind to Type II FcRs. Such variants, including a FA241 variant of SEQ ID NO: 1, represent species within a larger genus of molecules that, by virtue of mimicking the structural and biological properties of sialylated Fc, but do not require sialylation, can bind to Type II FcRs. See e.g., US20140377280, the content of which is incorporated by reference in its entirety. As disclosed US20140377280, such a variant lacks a polysaccharide chain having a terminal sialic acid connected to a galactose moiety through the α2,6 linkage at the aforementioned Asn297. Such non-sialylated IgG Fc variants may be expressed in a cell line.

In some example, the antibody/Fc-containing component of the immune complex can be artificially modified (e.g., pegylation and sialylation) to improve certain property of the complex, e.g., stability and binding to a receptor (such as Type II FcR).

In preferred embodiments, the antibody/Fc-containing component has an Fc that binds to or has enhanced binding to FcγRIIb (or other Type I FcRs). See, e.g., WO 2012/087928; Li & Ravetch (2011) Science 333:1030; Wilson et al. (2011) Cancer Cell 19:101; White et al. (2011) J. Immunol. 187:1754; and U.S. Pat. App. Pub. 2014/0010812. Such variants may provide an antibody with immunomodulatory activities related to FcγRIIb$^+$ cells, including for example B cells and monocytes. In one embodiment, the Fc variants provide selectively enhanced affinity to FcγRIIb relative to one or more activating receptors. Such variants may also exhibit enhanced FcR-mediated cross-linking, resulting in enhanced therapeutic efficacy. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y-267E, 236D-267E, 239D-268D, 239D-267E, 267E-268D, 267E-268E, and 267E-328F, Specifically, the S267E, G236D, S239D, L328F and I332E variants, including the S267E-L328F double variant, of human IgG1 are of particular value in specifically enhancing affinity for the inhibitory FcγRIIb receptor. Chu et al. (2008) *Mol. Immunol.* 45:3926; U.S. Pat. App. Pub. 2006/024298; WO 2012/087928. Enhanced specificity for FcγRIIb (as distinguished from FcγRIIa$_{R131}$) may be obtained by adding the P238D substitution and other mutations (Mimoto et al. (2013) *Protein. Eng. Des. & Selection* 26:589; WO 2012/1152410), as well as V262E and V264E (Yu et al. (2013) *J. Am. Chem. Soc.* 135:9723, and WO 2014/184545.

In certain embodiments, the Fc-containing component is modified to increase its biological half-life. Various approaches are possible and described in U.S. Pat. Nos. 8,629,113, 8,367,805, 7,867,491, 6,821,505, 6,277,375, 6,121,022, and 5,869,046, WO 2009/086320. WO 2006/130834. WO 2002/060919. WO 98/023289. WO 97/34631, Hinton et al., 2004, J. Biol. Chem. 279(8): 6213-6216, Hinton et al. 2006 Journal of Immunology 176:346-356), Shields et al, *Journal of Biological Chemistry* 2001, 276(9): 6591-6604), Dall'Acqua et al, *Journal of Immunology,* 2002, 169:5171-5180, Dall'Acqua et al., 2006, Journal of Biological Chemist 281:23514-23524), Yeung et al. (2009) *J. Immunol.* 182:7663), Zalevsky et al. (2010) *Nat. Biotechnol.* 28:157, Petkova et al. (2006) *Immunol.* 18:1759, Vaccaro et al. (2005) *Nat. Biotechnol.* 23:1283; and Yeung et al. (2010) *J. Immunol.* 182:7663-7671.

The serum half-life of the Fc-containing component of the present invention can also be increased by pegylation. An antibody can be pegylated to, for example, increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

2B. Antigenic Component

The skilled artisan will also understand that there are no limitations on the identities of the antigenic components in the immune complexes of the present invention. The immune complex discussed herein can be designed to contain any antigenic agent, antigen, immunogen, or epitope of interest. The antigen may contain a protein, a polypeptide, a peptide, an epitope, a hapten, or any combination thereof. The antigen can also contain a whole organism, killed, attenuated or live; a subunit or portion of an organism; a recombinant vector containing an insert with immunogenic properties; a piece or fragment of DNA capable of inducing an immune response upon presentation to a host animal. Alternately, the immunogen or antigen may contain a toxin or antitoxin.

In certain embodiments the antigenic component can come from a disease-causing microorganism. For example, it can be antigen or epitope from a virus of any one of the virus families: Adenoviridae (e.g., Adenovirus, infectious canine hepatitis virus), Papovaviridae (e.g., Papillomavirus, polyomaviridae, simian vacuolating virus), Parvoviridae (e.g., Parvovirus B19, canine parvovirus), Herpesviridae (e.g., Herpes simplex virus, varicella-zoster virus, cytomegalovirus, Epstein-Barr virus), Poxviridae (e.g., Smallpox virus, cow pox virus, sheep pox virus, orf virus, monkey pox virus, vaccinia virus), Hepadnaviridae (e.g., Hepatitis B virus), Anelloviridae (e.g., Torque teno virus), Reoviridae (e.g., Reovirus, rotavirus), Picornaviridae (e.g., Enterovirus, rhinovirus, hepatovirus, cardiovirus, aphthovirus, poliovirus, parechovirus, erbovirus, kobuvirus, teschovirus, coxsackie), Caliciviridae (e.g., Norwalk virus), Togaviridae (e.g., Rubella virus, alphavirus), Arenaviridae (e.g., Lymphocytic choriomeningitis virus), Flaviviridae (e.g., Dengue virus, hepatitis C virus, yellow fever virus), Orthomyxoviridae (e.g., Influenzavirus A, influenzavirus B, influenzavirus C, isavirus, thogotovirus), Paramyxoviridae (e.g., Measles virus, mumps virus, respiratory syncytial virus, Rinderpest virus, canine distemper virus), Bunyaviridae (e.g., California encephalitis virus, hantavirus), Rhabdoviridae (e.g., Rabies virus), Filoviridae (e.g., Ebola virus, Marburg virus), Coronaviridae (e.g., Corona virus), Astroviridae (e.g., Astrovirus), Bornaviridae (e.g., Borna disease virus), Arteriviridae (e.g., Arterivirus, equine arteritis virus), and Hepeviridae (e.g., Hepatitis E virus).

In a preferred embodiment, the antigen is a HA protein derived from an influenza virus to elicit flu immunity, especially pan-flu immunity. Other influenza epitopes or proteins, such as the neuraminidase (NA), can be used to elicit immunity to various distinct influenza types or other epitopes of viral origin.

Additional examples of suitable antigens, epitopes, or immunogenic moieties include prion, bacterial, or parasitic antigens; inactivated viral, tumor-derived, protozoal, organism-derived, fungal, or bacterial antigens; toxoids, toxins; self-antigens; polysaccharides; lipids, fatty acids, proteins; glycoproteins; peptides; cellular vaccines; DNA vaccines; recombinant proteins; glycoproteins; and the like, for use in eliciting immune response to, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus and yellow fever, and Alzheimer's Disease. Especially, materials (such as recombinant proteins, glycoproteins, peptides, and haptens) that otherwise do not raise a strong immune response can be used in connection with the invention so as to elicit satisfactory response.

In some embodiments, the epitope can be a portion of a cancer antigen, such that antibodies against the epitope can raise specific anti-cancer immunity. This will be particularly interesting in situations where passive infusion of specific antibodies is known to be therapeutic (as is the case with neurofibromatosis, a childhood cancer), or where specific anti-tumor antibodies can bind to receptors present in certain cancer tissues (e.g. breast) and inhibit cancer growth (e.g. Trastuzumab/herceptin, broadly used in breast cancer treatment to block neu/her receptors).

The terms cancer antigen and tumor antigen are used interchangeably and refer to an antigen that is differentially expressed by cancer cells. Cancer antigens can be exploited to differentially target an immune response against cancer cells, and stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-0017-1A/GA733, Carcinoembryonic Antigen (CEA) and its antigenic epitopes CAP-1 and CAP-2, etv6, am11, Prostate Specific Antigen (PSA) and its antigenic epitopes PSA-1, PSA-2, and PSA-3, prostate-specific membrane antigen (PSMA), T-cell receptor/CD3-ζ chain, MAGE-family of tumor antigens (e.g., MAGE-A1 MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, am11, cyclophilin b), B cell lymphoma (Ig-idiotype), glioma (E-cadherin, .alpha.-catenin, .beta.-catenin, gamma-catenin, and p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (.alpha.-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

Each of the above-described polypeptide/protein components of the immune complex can be obtained as a recombinant polypeptide/protein. To prepare a recombinant polypeptide, a nucleic acid encoding it (e.g., SEQ ID NO: 1) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the peptides/polypeptides/proteins of the invention can be chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The peptide/polypeptide/protein of this invention covers chemically modified versions. Examples of chemically modified peptide/protein include those subjected to conformational change, addition or deletion of a sugar chain, and those to which a compound such as polyethylene glycol has been bound. Once purified and tested by standard methods or according to the methods described in the examples below, the peptide/polypeptide/protein can be included in a pharmaceutical composition.

Compositions

The immune complex of the invention may be used in an immunogenic composition to immunize an animal. An immunogenic composition according to the invention is preferably used for the preparation of a vaccine. Preferably a prophylactic and/or therapeutic vaccine is produced. Thus, within the scope of this invention is an immunogenic or vaccine composition that contains a pharmaceutically acceptable carrier and an effective amount of an immune complex described above. The carriers used in the composition can be selected on the basis of the mode and route of administration, and standard pharmaceutical practice.

The composition can also contain an adjuvant. Examples of an adjuvant include a cholera toxin, Escherichia coli heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

A vaccine formulation may be administered to a subject per se or in the form of a pharmaceutical or therapeutic composition. Pharmaceutical compositions containing an immune complex of the invention and an adjuvant may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For injection, vaccine preparations may be formulated in aqueous solutions, preferably in physiologically compatible buffers such as Hanks' solution, Ringer's solution, phosphate buffered saline, or any other physiological saline buffer. The solution may contain formulatory agents such as suspending, stabilizing and/or dispersing agents. Alternatively, the immune complex escribed above may be in powder form for constitution with a suitable vehicle, e.g., sterile pyrogen-free water, before use.

The amount of a composition administered depends, for example, on the particular antigen in the composition, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the subject, but will typically range from about 0.1 mL to about 5 mL. Sera can be taken from the subject for testing the immune response or antibody production elicited by the composition against the antigen. Methods of assaying antibodies against a specific antigen are well known in the art. Additional boosters can be given as needed. By varying the amount of the composition and frequency of administration, the protocol can be optimized for eliciting a maximal production of the antibodies.

A composition of this invention can be administered parenterally, orally, nasally, rectally, topically, or buccally. A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils can be conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. When aqueous suspensions or emulsions are administered orally, the active ingredient can be suspended or dissolved in an oily phase combined with emulsifying or suspending agents. If desired, certain sweetening, flavoring, or coloring agents can be added.

Uses

The immune complex and composition disclosed herein can be used as an antibody stimulating platform, to raise antibodies against any antigenic agent, antigen, immunogen, or epitope of interest. The immune complex and composition of the invention can therefore be used as a prophylactic vaccine and therapeutic vaccine for treating various conditions. The complex/composition can be administered as the single therapeutic agent in a treatment regimen. Alternatively, it can be administered in combination with another therapeutic composition, or with other active agents such as antivirals, antibiotics, etc. In particular, the complex/composition of this invention can be useful for treating viral diseases and tumors. This immunomodulating activity suggests that the immunogenic or vaccine composition of the invention is useful in treating conditions such as, but not limited to:

(a) viral diseases such as diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as *chlamydia*, fungal diseases including but not limited to candidiasis, aspergillosis, histoplasmosis, cryptococcal meningitis, or parasitic diseases including but not limited to malaria, *Pneumocystis carnii* pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers.

In some embodiments, the immune complex or composition described herein can be used to elicit immunity against prion disease, whereby the immune complex contains a sequence of the prion protein (PrP) helix. The invention may therefore protect against Transmissible Spongiform Encephalopathies (TSEs, such as "mad cow disease" or scrapie in sheep), a disease of extensive veterinary interest. In yet another embodiment, the invention can be used to elicit immune responses to small molecule haptens that are drugs of abuse.

An additional use (particularly for the FcgRIIb-targeting IC) is depletion of antigen-specific B cells in autoimmune diseases via co-engaging B cell antigen receptor complex and Fcγ receptor IIb inhibitory receptor (Arthritis Rheumatol. 2014 May; 66(5):1153-64). Accordingly, this invention further provides a method of suppressing a population of B cells that are specific to a particular antigen. The method includes identifying subject in need thereof and administering to the subject an immune complex comprising the particular antigen (or antigenic section thereof) and an isolated protein. The protein comprises an IgG Fc region and is capable of binding to a Type II Fc receptor. Preferably, the protein is an antibody or an Fc region-containing fragment thereof. In one embodiment, the protein comprises a sialylated form of an IgG heavy chain (e.g., SEQ ID NO: 1 listed below) or an Fc region-containing fragment thereof. The ICs and methods can be used to treating various autoimmune diseases.

For example, in patients with acquired hemophilia A due to production of antibodies against Factor VIII, an immune complex comprising Factor VIII protein and anti-Factor VIII mAb with Fc domain enhanced for FcgRIIb binding can be used to suppress Factor VIII-specific B cells. A Factor VIII-Fc domain fusion protein can also be used for this purpose.

Definitions

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation). The Fc-containing peptide, polypeptide, or protein of this invention include recombinantly or synthetically produced fusion versions having the particular domains or portions that bind to Type II FcR, such as DC-SIGN. The term also encompasses polypeptides that have an added amino-terminal methionine (useful for expression in prokaryotic cells).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

A "human" antibody" refers to an antibody having variable regions in which both the framework and CDR regions are derived from human germline immunoglobulin sequences. Furthermore, if the antibody contains a constant region, the constant region also is derived from human germline immunoglobulin sequences. Human antibodies of the present invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody, e.g. a mouse antibody, are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody. A "hybrid" antibody refers to an antibody having heavy and light chains of different types, such as a mouse (parental) heavy chain and a humanized light chain, or vice versa.

As used herein, "antibody fragments", may comprise a portion of an intact antibody, generally including the antigen binding and/or variable region of the intact antibody and/or the Fc region of an antibody which retains FcR binding capability. Examples of antibody fragments include linear antibodies; single-chain antibody molecules; and multispecific antibodies formed from antibody fragments. Preferably, the antibody fragments retain the entire constant region of an IgG heavy chain, and include an IgG light chain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises $C_{H2}$ and $C_{H3}$ constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 of, for example SEQ ID NO. 1 above, (or an amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, Md.; see also FIGS. 3c-3f of U.S. Pat. App. Pub. No. 2008/0248028. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG (including a C-terminal lysine). As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 70% homology with a native sequence Fc region and/or with an Fc region of a parent polypeptide, and more preferably at least about 90% homology therewith, more preferably at least about 95% homology therewith, even more preferably, at least about 99% homology therewith.

"Antigenic agent," "antigen," or "immunogen" means a substance that induces a specific immune response in a host animal. It can be a molecule containing one or more epitopes (either linear, conformational or both) that elicit an immunological response. The term "epitope" refers to basic element or smallest unit of recognition by an individual antibody, B-cell receptor, or T-cell receptor, and thus the particular domain, region or molecular structure to which said antibody or T-cell receptor binds. An antigen may consist of numerous epitopes while a hapten, typically, may possess few epitopes.

The term "immunogenic" refers to a capability of producing an immune response in a host animal against an antigen or antigens. This immune response forms the basis of the protective immunity elicited by a vaccine against a specific infectious organism. "Immune response" refers to a response elicited in an animal, which may refer to cellular immunity (CMI); humoral immunity or both.

As used herein, the terms "specific binding," "selective binding," "specific for," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., HA, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model. The term "animal" includes all vertebrate animals including humans. In particular, the term "vertebrate animal" includes, but not limited to, humans, canines (e.g., dogs), felines (e.g., cats); equines (e.g., horses), bovines (e.g., cattle), porcine (e.g., pigs), as well as in avians.

As used herein, "treating" or "treatment" (e.g., a viral infection, tumor or cancer) refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder. When the terms "prevent", "preventing", and "prevention" are used herein in connection with a given treatment for a given condition, they mean that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have "prevented" the condition if it is given during exposure of a patient to a stimulus that would have been expected to produce a given manifestation of the condition, and results in the patient's experiencing fewer and/or milder symptoms of the condition than otherwise expected. For example, a treatment can "prevent" infection by resulting the patient's displaying only mild overt symptoms of the infection; it does not imply that there must have been no penetration of any cell by the infecting microorganism.

An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment. A therapeutically effective amount to treat or inhibit a viral infection is an amount that will cause a reduction in one or more of the manifestations of viral infection, such as viral lesions, viral load, rate of virus production, and mortality as compared to untreated control animals. A therapeutically effective amount of a combination to treat a neoplastic condition is an amount that will cause, for example, a reduction in tumor size, a reduction in the number of tumor foci, or slow the growth of a tumor, as compared to untreated animals.

The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

EXAMPLES

Example 1

This example describes general materials and methods used in the examples below.

Clinical Studies

The 2012-2013 TIV vaccination study was conducted at the Rockefeller University Hospital in New York City in accordance with a protocol approved by the Institutional Review Board of Rockefeller University (protocol #TWA-0804), in compliance with guidelines of the International Conference on Harmonization Good Clinical Practice guidelines, and was registered on www.clinicaltrials.gov (NCT01967238). Samples were drawn from 10 healthy adult volunteers (FIG. 8). B cells analyzed for gene expression derived from donors as part of a study approved by the Emory University institutional review board (IRB #00022916). Healthy volunteers received the 2009-2010 trivalent inactivated influenza vaccine. All samples were processed within 30 minutes of being drawn; sera and PBMCs were stored at −80° C. and were thawed once prior to analysis.

Recombinant Proteins and Generation of Immune Complexes

Recombinant anti-HA mAb PY102 was expressed as a human IgG1 in 293T cells stably expressing human ST6GAL1 and B4GALT1 and purified using protein G chromatography as previously described (Bournazos et al. (2014) Cell 158, 1243-1253). HA proteins were expressed in a baculovirus system as previously described (Pica et al. (2012) Proceedings of the National Academy of Sciences of the United States of America 109, 2573-2578). ICs were formed by incubation of molar ratio 30:1 (polyclonal human) or 3:1 (PY102) IgG:HA trimer for 1 h at 4° C. IgG subclass and Fc glycan composition were determined by mass spectrometry; size of ICs was determined by size exclusion chromatography (See extended supplemental procedures for detailed protocols).

Fc Glycan Analysis

HA-specific IgGs were isolated from serum-purified IgG by HA affinity chromatography and their Fc-associated glycans were analyzed by tryptic digestion followed by mass spectrometry.

More specifically, HA-specific IgGs were isolated from serum-purified IgG by HA affinity chromatography for mass spectrometric analysis of Fc glycoforms. Protein samples (10 µg) were denatured with 6M guanidine-HCl, reduced with 10 mM DTT at 56° C. for 45 min and alkylated with 60 mM iodoacetamide for 1 h followed by 30 min incubation with 20 mM DTT. The samples were trypsin digested (37° C. for 16 h) and desalted using solid phase extraction (SPE) on Sep-Pak Cartridges (Waters, Milford, Mass.). Tryptic peptides were eluted and evaporated to dryness in a Speed-vac SC110 (Thermo Savant) before analysis. Fc glycoforms were specifically identified (Fab glycans excluded) based on tryptic peptide sequence identification. NanoLC-MS/MS analysis for characterization of glycosylation sites was performed on an UltiMate3000 nanoLC (Dionex) coupled with a hybrid triple quadrupole linear ion trap mass spectrometer, the 4000 Q Trap (AB SCIEX).

MS data acquisition was performed using Analyst 1.4.2 software (Applied Biosystems) for precursor ion scan triggered information dependent acquisition (IDA) analysis and enhanced MS-based IDA analysis (Zhang et al. (2012) Proteomics 12, 1269-1288; and Zhang et al. (2005) JBT 16, 209-219). The precursor ion scan of the oxonium ion (HexNAc+ at m/z 204.08) was monitored at a step size of 0.2 Da across a mass range of m/z 400 to 1600 for detecting glycopeptides containing N-acetylhexosamine unit. The nanospray voltage was 1.9 kV, and was used in positive ion mode for all experiments. The declustering potential was set at 50 eV and nitrogen as collision gas. In IDA analysis, after each precursor ion scan or EMS scan, and enhanced resolution scan, the two to three highest intensity ions with multiple charge states were selected for tandem MS (MS/MS) with rolling collision energy applied for detected ions based on different charge states and m/z values. All acquired MS/MS spectra from EMS-IDA were subjected to Mascot database search. All acquired MS/MS spectra for detected glycopeptides ions by precursor ion scanning were manually inspected and interpreted with Analyst 1.4.2 and BioAnalysis 1.4 software (Applied Biosystems). The peak areas of detected precursor ions were determined by extracted chromatogram (XIC) at each specific m/z representing glycopeptides isoforms. The relative quantitations of the sugar glycan isoforms of N-linked peptide ions were carried out based on precursor ion peak areas under assumption that all sugar glycan isoforms linked to the same core peptide have identical or a similar ionization efficiency. The eleven glycoforms analyzed were those present in greatest abundance within the sample set.

ELISAs

HA ELISAs were performed as described previously (Wang et al. (2010) PLoS pathogens 6, e1000796). Negative control (naïve mouse serum or binding values of human IgGs on the irrelevant protein bovine serum albumin) values were subtracted from readings given by test samples. Study subjects were determined to have positive IgG binding titers when binding was five times above background. For affinity ELISAs, sera diluted 1:200 were incubated on plates coated with 1 ug/mL HA protein (low density) or 6 ug/mL HA (high density). The affinity of HA-specific IgG was expressed as a ratio of binding to low density:high density HA-coated plates. This method was adapted from the well-established assay used for measurement of polyclonal anti-nitrophenyl-hapten affinity (Herzenberg et al. (1980) The Journal of experimental medicine 151, 1071-1087).

Flow Cytometry Analysis

Plasmablasts (PB) were identified by FACS from PBMCs as CD19$^+$, CD3$^-$, CD20$^{lo}$, CD38$^{hi}$, CD27$^{hi}$, CD138$^-$; memory cells were identified as CD19$^+$, CD3$^-$, CD20$^+$, CD38$^+$, CD27$^+$, CD138$^-$. Glycosyltransferase levels were determined using ST6Gal 1-FITC (USBiological) and FUT8-FITC (Bioss), both polyclonal rabbit IgGs (Abcam). A control polyclonal rabbit IgG-FITC antibody was used to determine background binding. Intracellular staining was performed using Cytofix/Cytoperm and Perm/Wash solution as recommended by the manufacturer (BD Biosciences).

Hemagglutination Inhibition Assay

Sera were tested in a standard hemagglutination inhibition assay (WHO/CDS/CSR/NCS/2002.5). Briefly, chicken red blood cells and 96-well V-bottom plates (Costar) were used. Influenza virus was diluted to 4 hemagglutination units/25 µl immediately before use in the HAI assay. Sera were treated with RDE (receptor-destroying enzyme) (Sigma Aldrich) per standard protocol prior to testing. HAI titer was defined as the reciprocal of the greatest dilution that completely inhibited hemagglutination of RBCs. HAI tests were performed twice, in duplicate.

Gene Expression

PBMCs were isolated 7 days post vaccination and PBs and memory cells were isolated by cell sorting. PBs were highly enriched for influenza vaccine-specific cells as demonstrated by ELISPOT. Immediately after sorting, RNA was isolated from approximately 200,000 plasma cells or PB or approximately 1,000,000 CD27+ B cells using the Qiagen RNEasy mini kit. RNA expression levels were determined using Illumina human-6 v2.0 expression beadchips at the Keck Microarray Resource at Yale. Six replicate RNA samples were analyzed for each cell type. Expression values were normalized for all samples using quantile normalization.

Size Exclusion Chromatography

ICs were generated by incubation of recombinant HA (molar ratio of 1:3 HA:IgG) with either monoclonal anti-HA PY102 or HA-specific IgG isolated from human plasma by affinity purification using recombinant HA. Size of the ICs was determined by size exclusion chromatography using a Superdex 200 10/300 GL column (GE healthcare) on an Akta Pure 25 HPLC system (GE Healthcare). A mix of proteins with varying MW (20-1236 kDa; NativeMark protein standard; Life technologies) was used for size calibration.

Generation and Characterization of Immune Complexes

The polyclonal human ICs were formed by incubation of molar ratio 30:1 polyclonal IgG:HA trimer. Subclass distribution in the IgG preparation was 74.9% IgG1, 20.4% IgG2, 4.5% IgG3, as determined by mass spectrometry. Fc glycoform composition without neuraminidase treatment was 4.2% afucosylated (G0, G1, G2), 17.69% sialylated (G1FS, G2FS), 78.0% neutral (G0F, G1F, G2F, G0FN, G1FN, G2FN). Size of the complexes was determined by HPLC; three peaks corresponding to immune complexes were observed in both the sialylated and asialylated preparations—peak 1: >600 kd, peak 2: ~537 kd, peak 3: ~445 kd. The monoclonal human ICs were generated by incubation of molar ratio 3:1 IgG1:HA trimer. Fc glycoform composition without neuraminidase treatment was 4.5% afucosylated (G0, G1, G2), 23.79% sialylated (G1FS, G2FS), 70.97% neutral (G0F, G1F, G2F, G0FN, G1FN, G2FN). Sialylated glycoforms were not detected following neuraminidase treatment. Size of the complexes was determined by HPLC; one peak corresponding to immune complexes of ~634 kD was observed in the sialylated and asialylated IC preparation.

Surface Plasmon Resonance Analysis

The binding properties of serum antibodies were analyzed by SPR (Biacore T-200. GE Healthcare). Protein G-purified serum IgG from vaccinated mice was immobilized to the surface of a CMS sensor chip (GE Healthcare) using amine coupling chemistry at a density of 1000 RU. Varying concentration (1 nM-50 nM) of either PR8-HA or cH5/1 HA were injected sequentially over flowcells of the sensor chip.

Samples were fit to heterogeneous ligand binding model and the off-rate constant (kd/s) was calculated.

In Vivo Studies

All mice were maintained in a specific-pathogen-free facility at the Rockefeller University and all studies were approved by the Rockefeller University Institutional Animal Care and Use Committee.

Polyclonal IC immunization: For mouse immunizations using human serum-derived ICs, A/California/04/2009 HA protein (10 ug) was delivered alone, or in complex with pooled, protein G-purified, week 3 post-vaccination IgG from vaccinated subjects. As control, asialylated IgG was prepared by treatment of IgG with α2-3,6,8 Neuraminidase as described (Anthony et al. (2011) Nature 475, 110-113) (New England Biolabs). Mice previously administered with ICs were boosted, intraperitoneally, at 3 wk intervals, with 10 ug HA in PBS or incomplete Freund's adjuvant (IFA) or complete Freund's adjuvant (CFA) (Sigma Aldrich) or Alum.

For in vivo neutralization studies, anesthetized mice (female C57BL/6J; 6-8 wk old) were infected intranasally with 5 mLD50 of the A/Netherlands/602/09 (H1N1) or cH5/1$_{PR8}$N1$_{PR8}$ virus (the HA contains a head domain derived from H5N1 strain A/Viet Nam/1203/04 and a stalk domain derived from H1N1 strain A/Puerto Rico/8/34—generated as described in (Hai et al. (2012) Journal of virology 86, 5774-5781)). IgGs from vaccinated mice were purified from pooled sera using protein G (GE Healthcare) and mixed with virus prior to intranasal infections. For the Netherlands/09 challenge, 10 ug/ml IgG was mixed with virus, for the cH5/1 challenge, 200 ug/ml IgG was used. Mouse body weight was recorded daily, and death was determined by a 20% body weight loss threshold.

Monoclonal IC Immunizations

For PY102 mAb immunizations, 20 ug PR8 HA and 50 ug PY102 or 20 ug PR8 HA alone was delivered intravenously to 6 wk old wild type or CD23$^{-/-}$ BALB/c mice. Boosts were administered as described above. For challenge studies, mice were anesthetized and infected as described above. A mixture of mouse-adapted virus (A/PR8/1934 (H1N1), A/FM/1/1947 (H1N1) or A/Netherlands/602/09 (H1N1) and purified polyclonal IgG (75 μg/mL) from vaccinated mice was pre-incubated at room temperature for 30 minutes. Six- to eight-week old female BALB/c mice were then infected with 5 mLD50 of virus. Mice were weighed daily to monitor morbidity and animals that exceeded 25% weight loss were euthanized.

Statistical Analysis

All data were analyzed in Prism 6 (GraphPad). Results from multiple experiments are presented as mean±SEM. Correlation analysis was used to determine the Pearson correlation coefficient, r. Linear regression was used to determine goodness of fit, $R^2$.

Two taile paired/unpaired student's t tests or ANOVA followed by Tukey posthoc analysis were performed to assess differences in the mean values of quantitative variables.

Example 2 Characterization of Fc Domain Structure on TIV-Elicited IgGs

Figures 8A, 8B:
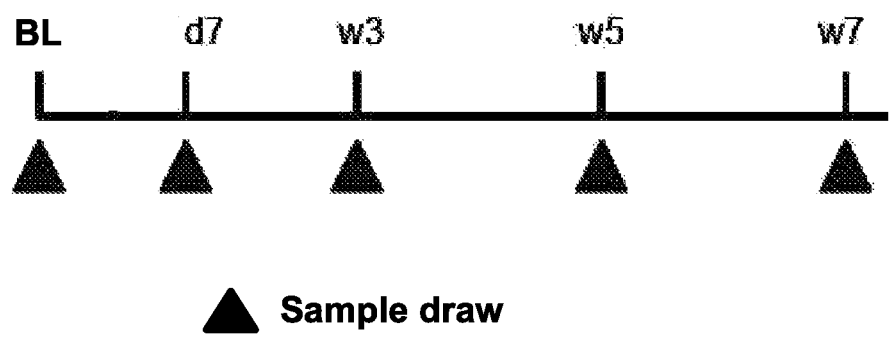
FIGS. 8A and 8B are diagrams showing study timeline and demographic data. (A) Sera and PBMCs were drawn prior to vaccination at baseline (BL), day 7, week 3, week 5 and week 7 post TIV administration. (B) Study demographics.
Figure 9A:
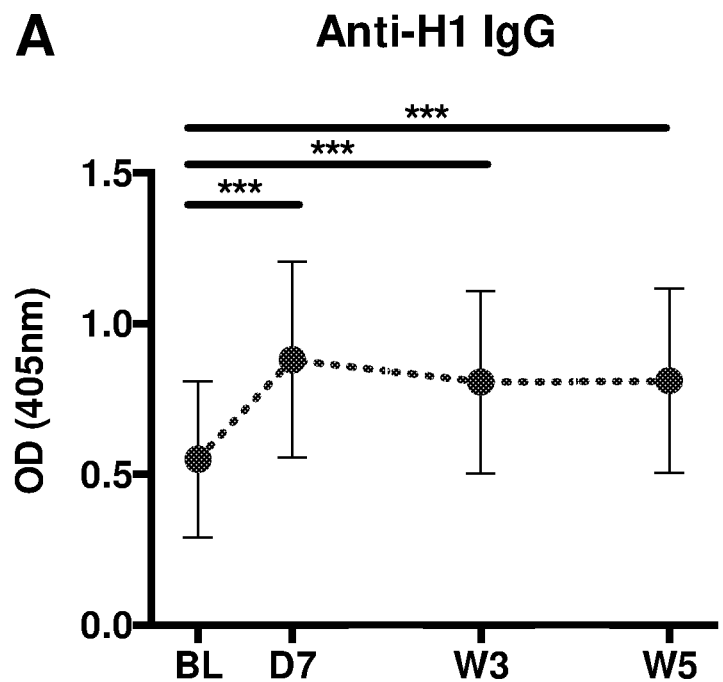
FIGS. 9A, 9B, 9C, 9D, 9E, 9F, and 9G are diagrams showing additional characterization of TIV response. Healthy adults were vaccinated with the 2012-2013 seasonal trivalent inactivated influenza virus vaccine. (A) At baseline, all subjects were positive for binding IgG against the H1 hemagglutinin vaccine component from the H1N1 A/California/04/2009 virus (the x-axis is not linear) and (B) HAI+ IgG. Titers were elevated by day 7 post vaccination. (C) Fc glycoforms on baseline anti-H1 IgG. Composition of the core Fc glycan can be modified by addition of fucose (F), N-acetylglucosamine (N), galactose (G) and sialic acid (S). Glycoforms are listed by modifications only—all Fc glycoforms contain the core structure of three mannose residues and four N-acetylglucosamine residues shown in the dotted box in FIG. 1d. (D) Anti-H1 IgG1 was significantly more sialylated (sFc) and (E) less fucosylated (fucFc) than total IgG1 from the same donors. (F) Anti-H1 IgG subclass distribution was not significantly different from the subclass distribution of total IgG. (G) Anti-globular head IgG were in greater abundance in most subjects than anti-stalk IgG at week 3 post vaccination.
Figure 9B:
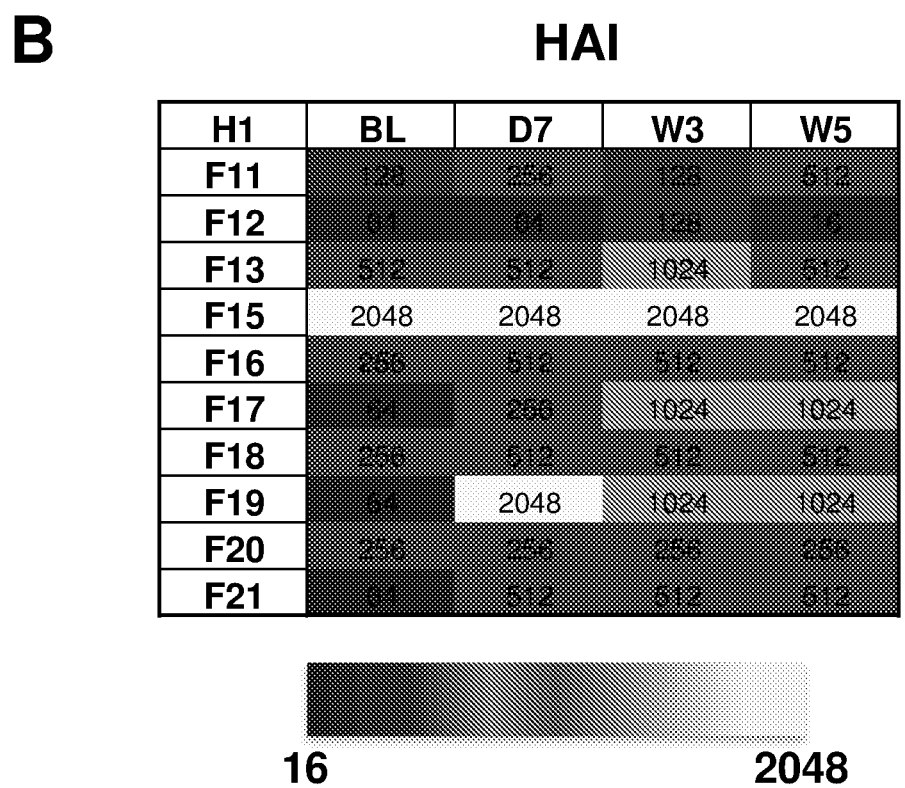
Figure 9C:
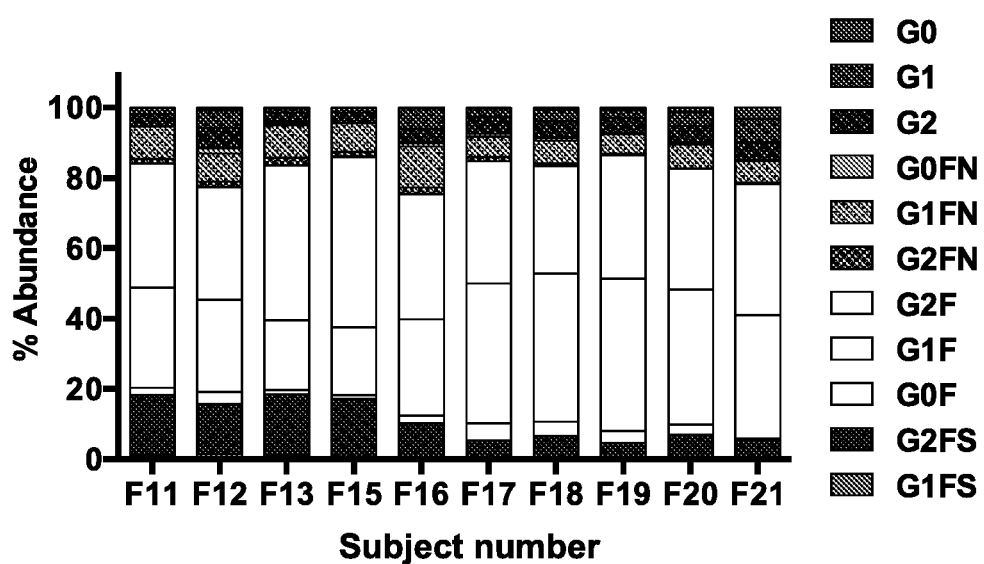
Figure 9D:
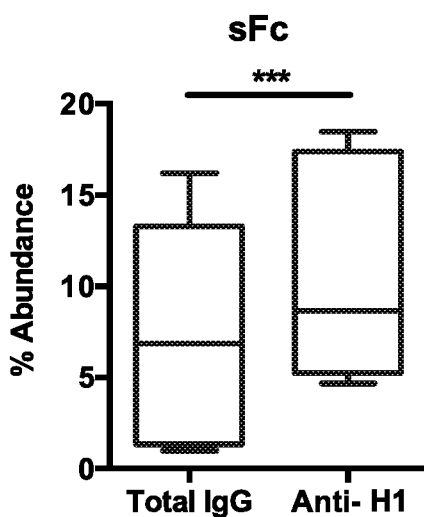
Figure 9E:
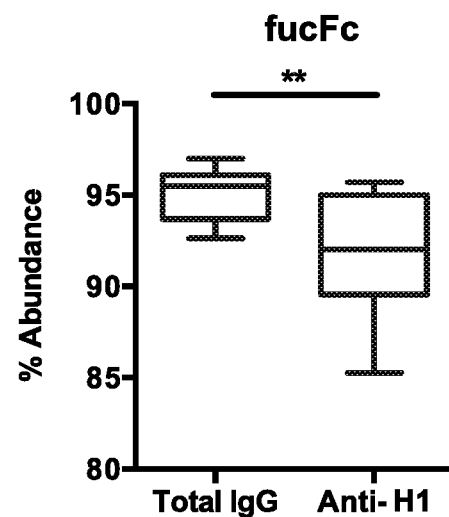
Figure 9F:
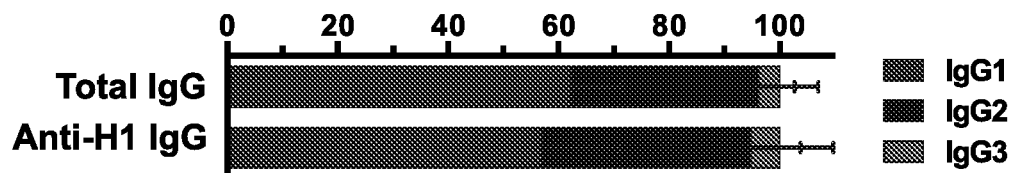
Figure 9G:
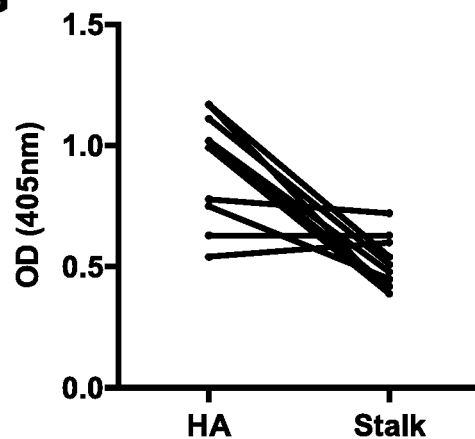

Healthy adults were vaccinated with the 2012-2013 TIV. Sera were drawn at baseline (pre-vaccination), day 7, week 3, week 5 and week 7 following vaccination and antigen-specific IgGs were isolated for subsequent analysis of Fc glycan composition and IgG subclass (FIG. 8a). At baseline, all subjects were positive for IgG against the H1 HA vaccine component, A/California/04/2009 (H1N1 virus), by H1-binding ELISA and the hemagglutination inhibition (HAI) test using homologous virus (FIG. 9a,b). Baseline anti-H1 IgG was characterized for subclass distribution and Fc glycan composition (FIG. 1b,e). Fc glycoforms on baseline anti-H1 IgG were predominantly neutral (G0F, G1F, G2F, G0FN, G1FN, G2FN), with an inter-subject range of 66.3-88.3% neutral glycans, bisecting GlcNAc (N) moieties (G0FN, G1FN, G2FN) were present with a range of 6.2-14.6%, sialylated glycoforms (G1FS, G2FS) were present with a range of 4.6-18.5% and afucosylated glycans (G0, G1, G2) were present with a range of 4.27-15.07% (FIG. 9c). Anti-H1 IgG at baseline contained significantly more sFc and less fucFc than total IgG, while subclass distribution was not different between H1-specific and total IgG (FIG. 9 d,e,f).

Following vaccination, modulations in the abundance of sFc glycoforms on H1-specific IgG were observed. Sialylated Fc glycoforms were significantly elevated and at peak abundance by day 7 post vaccination; this was mirrored by an increase in fucFc by day 7. Sialylated Fc glycoforms and fucFc on anti-H1 IgG were consistently elevated above pre-vaccination levels through week 7 except for a significant dip at week 3 post-vaccination (FIG. 2a,b).

Figures 2C, 2D:
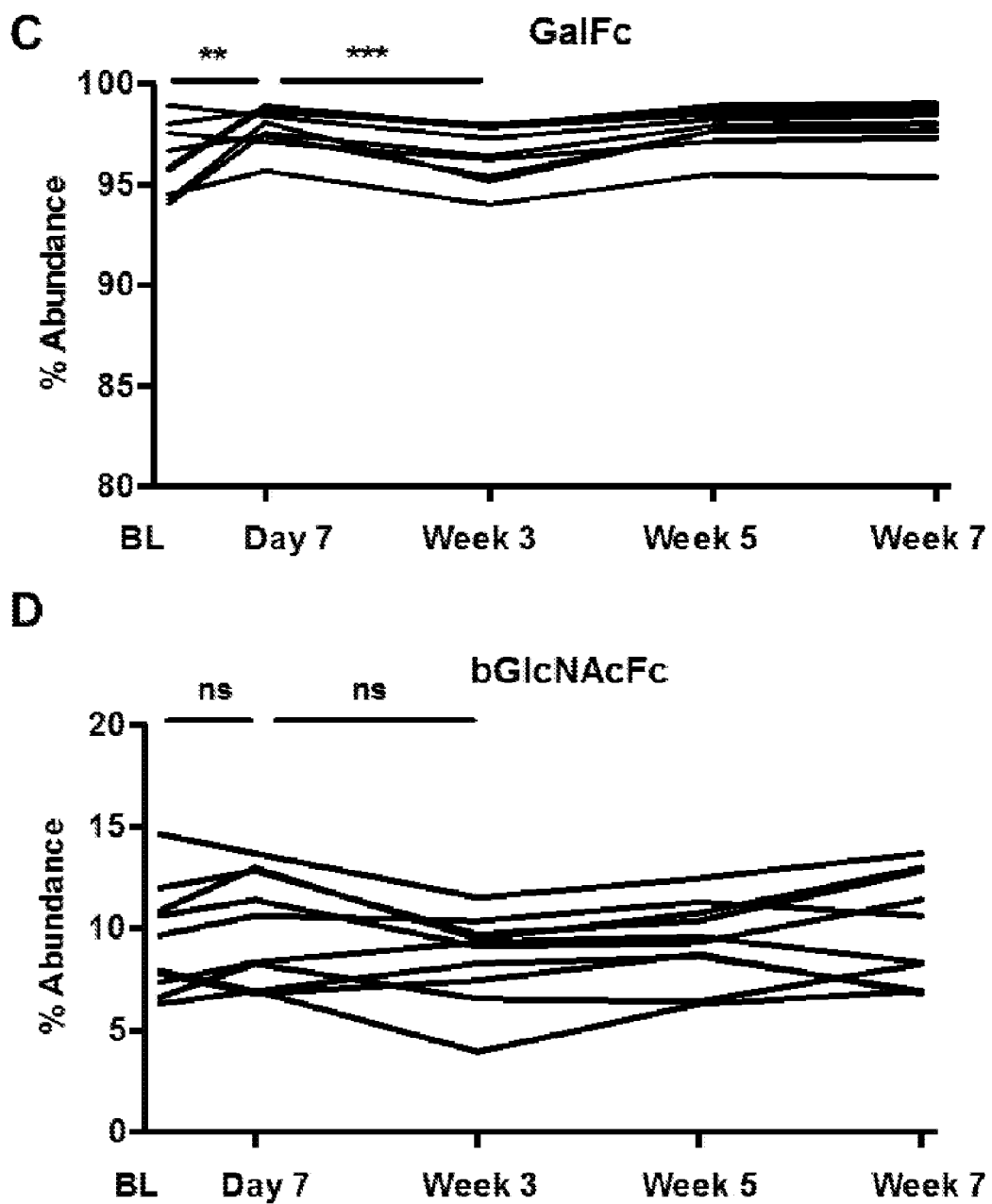

Because galactosylation is a prerequisite for sialylation of the Fc glycan, the presence of galactose could be a limiting factor in determining the abundance of subsequent sialic acid modification. Analysis showed that galactose (GalFc) levels were modulated to a small, but statistically significant degree following vaccination, but that the overall abundance of galactosylated glycans was over 90% in all subjects at every timepoint (FIG. 2c). This was several fold higher than sialylated glycans, suggesting that galactosylation was not limiting and that modulations in sialylation were independently regulated. There was no apparent regulation of bisected GlcNac glycoforms (bGlcNAcFc) following vaccination (FIG. 2d).

Figures 2E, 2F, 2G:
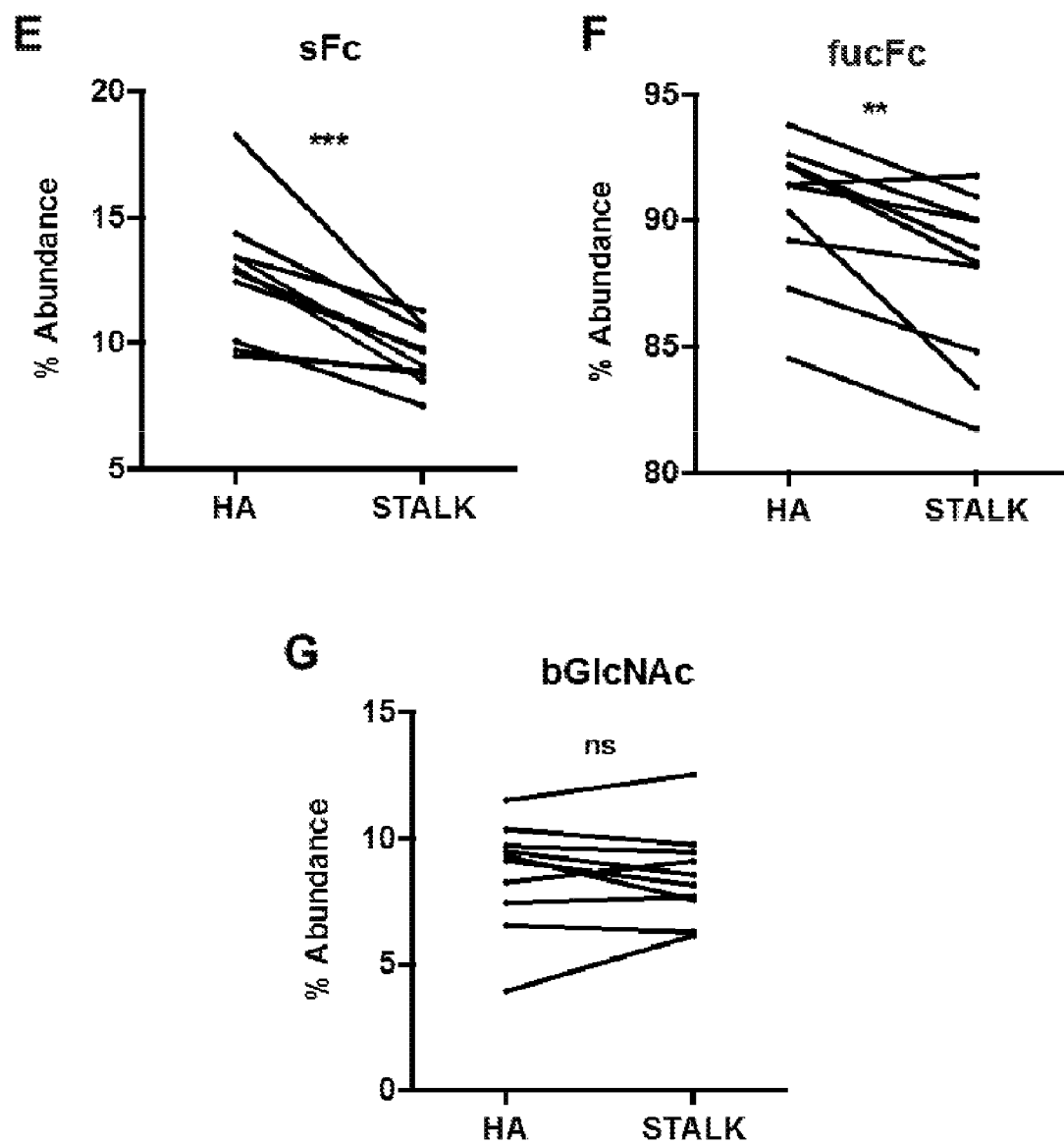

In addition to regulation of Fc glycoforms over time following vaccination, analysis of HA-specific IgG from a single timepoint, week 3, revealed that specific Fc glycoforms can be linked to Fab specificity, possibly due to differential glycosylaytion by distinct IgG-producing B cell subsets such as plasmablasts (PB) and memory B cells. Anti-HA IgG (predominantly globular head-specific) (FIG. 9g) and anti-HA stalk IgG differed significantly in Fc glycoform profile, with sialylated, fucosylated glycan levels highest on anti-HA globular head IgG and lowest on anti-HA stalk IgG (FIG. 2e,f). No differences were observed in levels of bisecting GlcNAc between total HA and stalk-specific IgG (FIG. 2g).

Figure 3A:
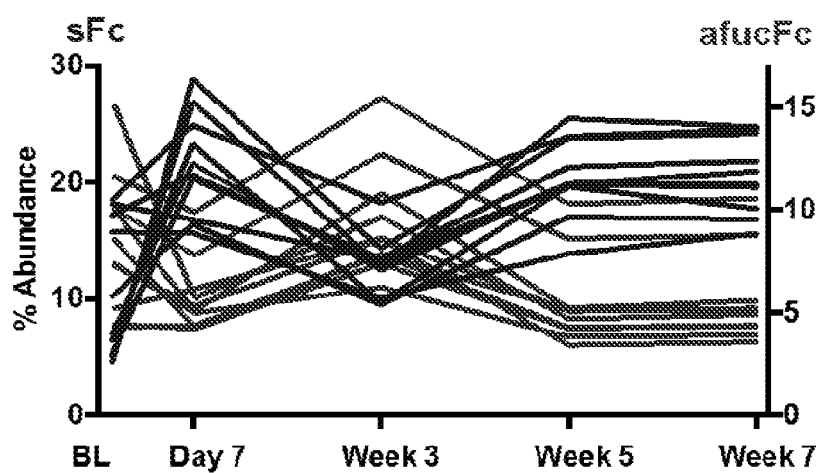
FIGS. 3A and 3B are a set of diagrams showing activating Fc glycan composition at week 3 post vaccination is mirrored by activating IgG subclass distribution. (A) Fc glycoforms at week 3 post vaccination were high in afucFc content. (B) This activating Type 1 FcR binding glycoform profile was mirrored by a peak in IgG1 subclass at week 3 post vaccination. Relative IgG subclass distribution was determined by mass spectrometric quantification of subclass specific tryptic peptides. IgG4 was not in sufficient abundance to quantify accurately. $*p<0.05$; $p<0.01$; $*p<0.001$; $****p<0.0001$ determined by the Tukey post-hoc test.
Figure 3B:
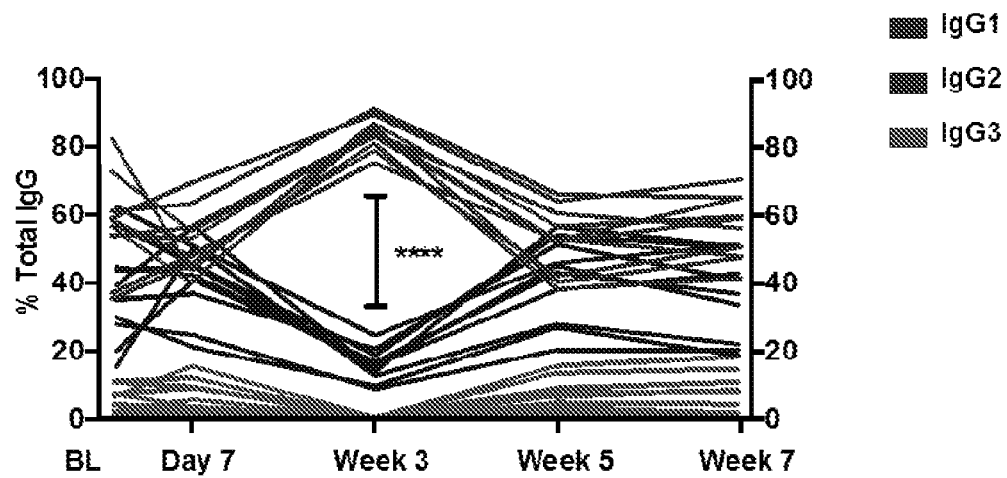

Day 7 post vaccination was characterized by an increase in sFc on anti-H1 IgG, which would increase Type II FcR binding by ICs. In contrast, week 3 post vaccination was characterized by diminished sFc and elevated afucFc, which would shift the signaling balance towards Type I FcRs (FIG. 3a). In addition to modulations in Fc glycan composition following vaccination, changes in subclass distribution of anti-HA IgG were observed. IgG1, which binds activating Type I FcRs when modified by an asialylated Fc glycoform, comprised a median abundance of 35.2% of total anti-H1 IgG at baseline, but peaked to a median level of 75.18% by week 3 (FIG. 3b). This activating IgG subclass distribution at week 3 paralleled the peak in activating, afucosylated Fc glycoforms and diminished sialylated glycoforms, all of which would contribute toward a shift in IC binding toward activating Type I FcRs (FIG. 3a,b).

Figures 10A, 10B, 10C:
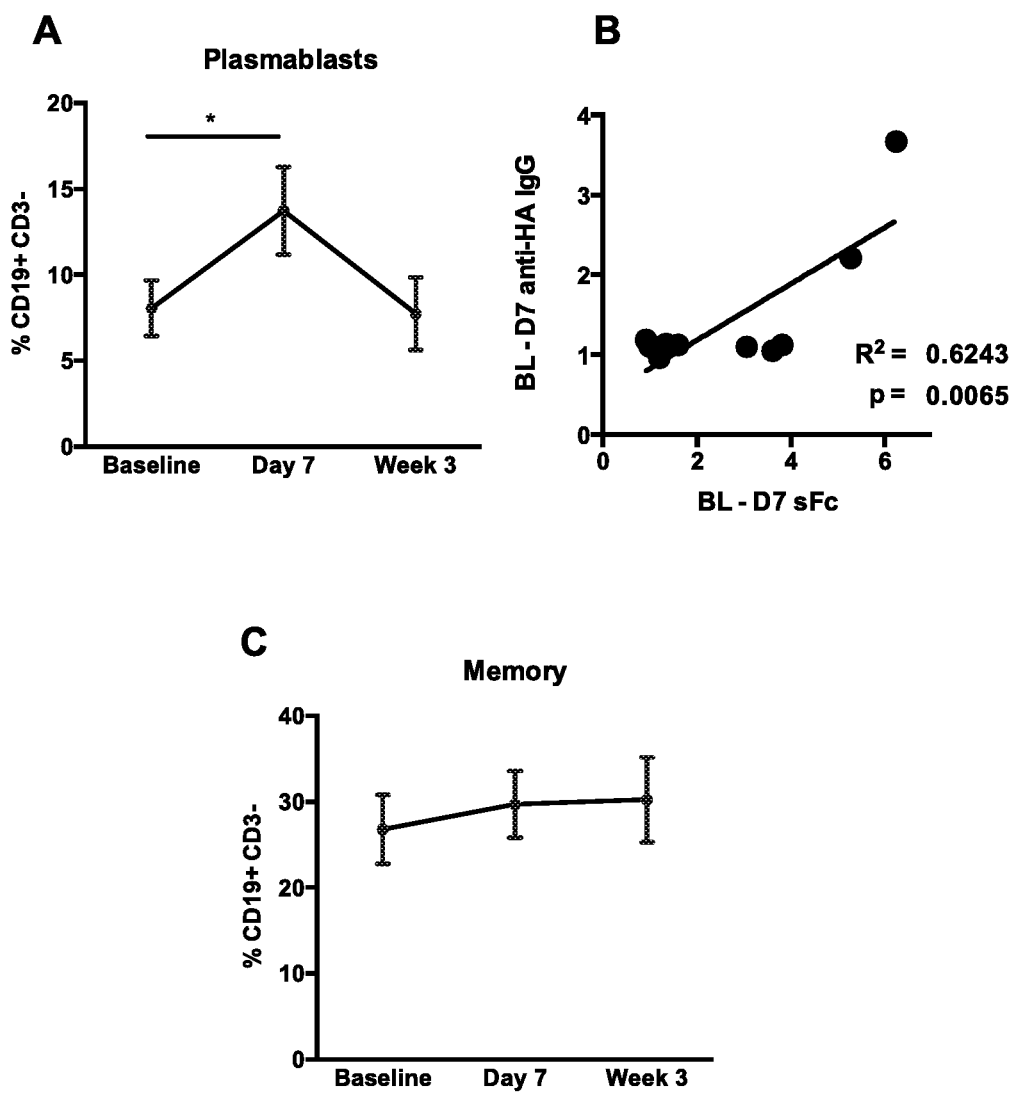
FIGS. 10A, 10B, 10C, 10D, 10E, 10F, 10G, and 10H are diagrams showing glycosyltransferase expression in activated B cell subsets. (A) PB peaked at day 7 post vaccination. (B) Change in abundance of sFc on anti-HA IgG correlated with change in anti-IgG titer by day 7 post vaccination. (C) Memory B cells increased in abundance through week 3 post vaccination. (D) B cells from 3 cohort subjects were analyzed for glycosyltransferase expression. ST6Gal1 expression was higher in PB (PB) than in memory cells. (E) Elevation in plasmablast FUT8 expression did not reach statistical significance. (F,G) ST6Gal1 and FUT8 transcript abundance was greater in PB than in memory cells. (H) No difference in B4GALT1 transcript level was observed between PB and memory cells. $*p<0.05$; $p<0.01$; $*p<0.001$; $****p<0.0001$ determined by two-tailed student's t test. Correlation analysis was used to determine the Pearson correlation coefficient, r. Linear regression was used to determine goodness of fit, $R^2$.
Figures 10D, 10E, 10F, 10G, 10H:
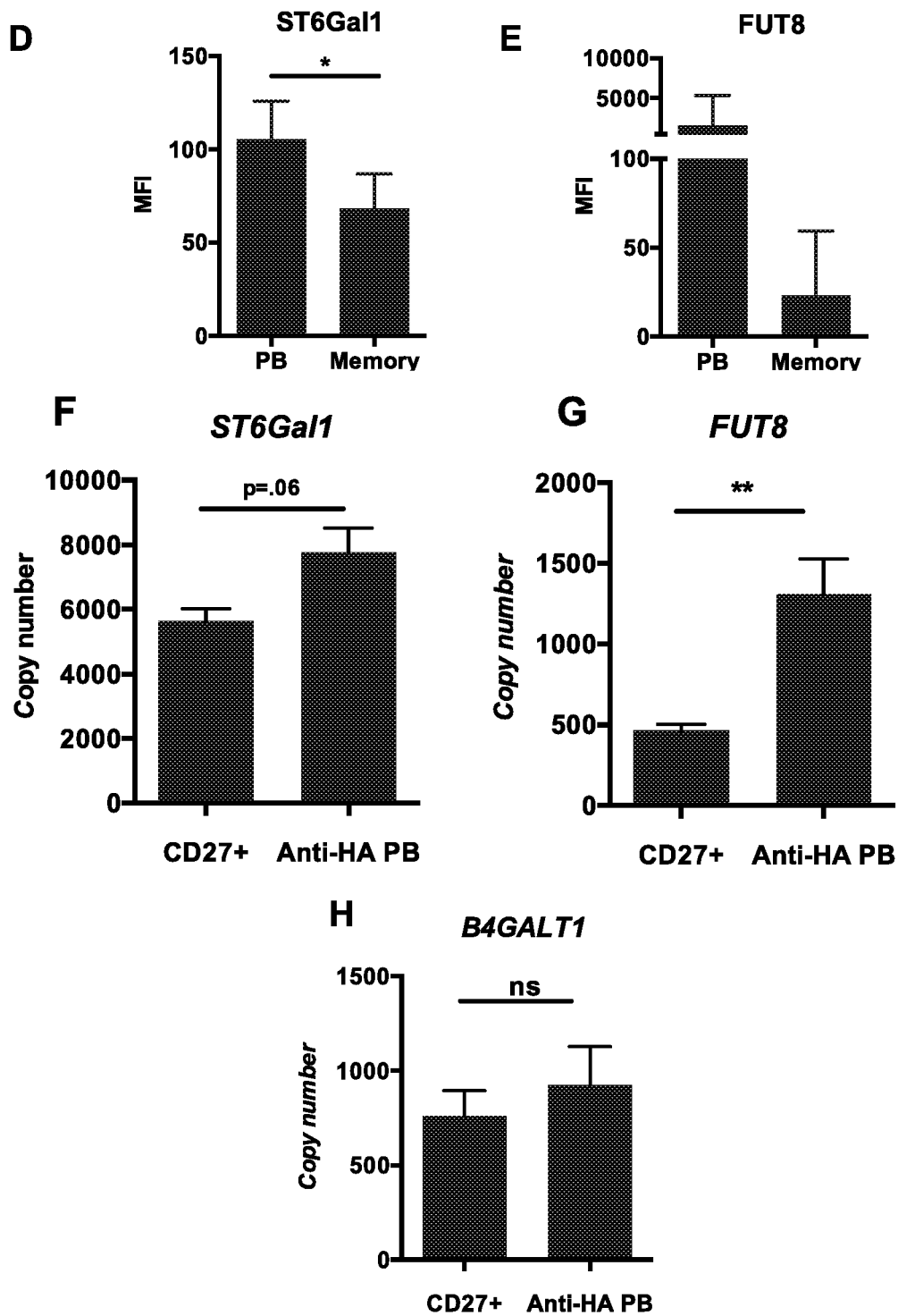

Example 3 Fc Glycoforms Present Following Vaccination Mirror Glycosyltransferase Expression in Activated B Cell Subsets Peak levels of sialylated and fucosylated Fc glycans at day 7 post-vaccination mirrored a peak in plasmablast abundance in the peripheral blood of the study subjects, in accordance with the well-described kinetics of plasmablast expansion that occurs following TIV administration (FIG. 10a) (Wrammert et al. (2011) The Journal of experimental medicine 208, 181-193; and Wrammert et al. (2008) Nature 453, 667-671). In addition, the amount of anti-H1 IgG produced during the early plasmablast response correlated with the change in sFc abundance on anti-HA IgG in the first 7 days following vaccination (p=0.0065) (FIG. 10b). These observations led to a hypothesis that sialylated and afucosylted Fc glycoforms may be produced, at least in part, by PB. Because the increase in relative abundance of afucFc and asialylated Fc glycoforms at week 3 mirrored an increase in peripheral memory B cells in the patient cohort (FIG. 10c), as has also been described in Pinna et al. (2009) European journal of immunology 39, 1260-1270, it was hypothesized that that those glycoforms may derive from memory B cells. Intracellular staining of PB and memory B cells for the relevant glycosyltransferases, ST6Gal1 and FUT8, revealed increased ST6Gal1 expression and non-significantly increased FUT8 expression in PB over memory B cells (FIG. 10d,e). In addition, gene analysis of day 7 PB and memory B cells from patients who received the 2009-10 TIV revealed elevated levels of ST6Gal1 (p=0.06) and FUT8 (p=0.006) in PB (FIG. 10f,g). Unlike ST6Gal1 and FUT8, B4GALT1, coding for a galactosyltransferase involved in Fc glycan modification, was not significantly elevated (FIG. 10h).

Figure 4A:
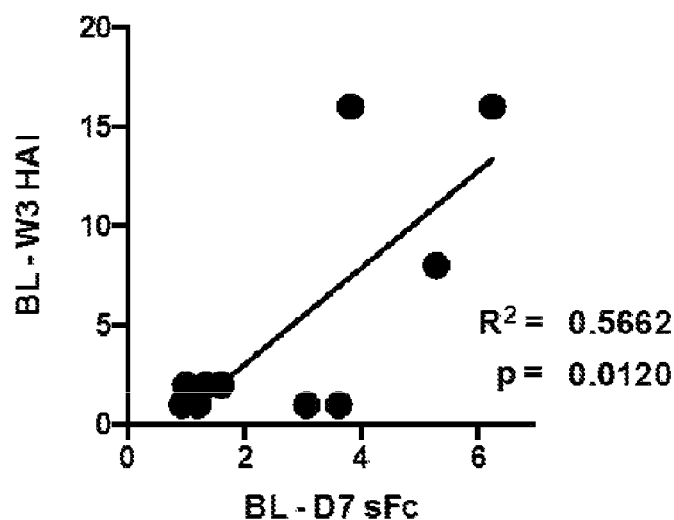
FIGS. 4A and 4B are a set of diagrams showing sialylated Fc abundance predicts influenza virus vaccine efficacy. (A) Abundance of sialylated glycoforms on anti-HA IgG produced in the first week post vaccination (Week 1 sFc) predicts change in HAI titer from baseline to week 3 post vaccination (Week 3 HAI). (B) In addition, sialylated glyco form abundance at week 3 post vaccination (% sFc) predicted affinity of anti-HA IgG at week 3 post vaccination (anti-HA affinity). Correlation analysis was used to determine the Pearson correlation coefficient, r. Linear regression was used to determine goodness of fit, $R^2$.
Figure 4B:
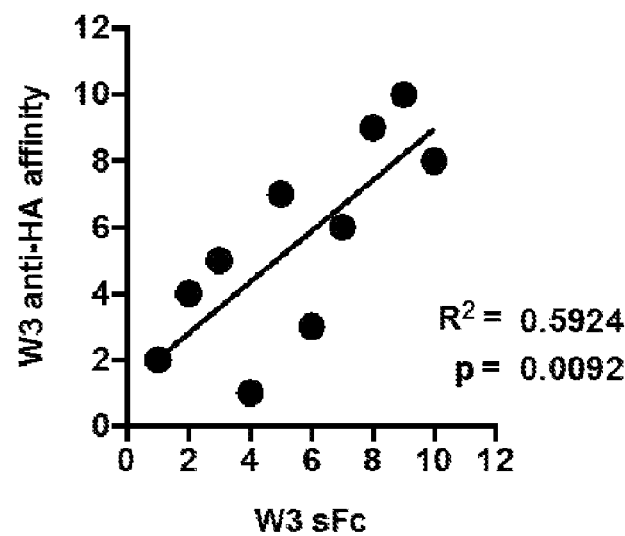

Example 4 Sialylated Fc Abundance Predicts Influenza Virus Vaccine Efficacy, as Defined by Change in HAI+ Titer Post Vaccination To investigate the significance of these regulated changes in Fc glycan composition and IgG subclass distribution following TIV vaccination, assays were carried out to examine the impact of these changes on hemagglutination inhibition, a commonly used measure of TIV vaccine efficacy. In particular, since the degree of HA-specific plasmablast expansion on day 7 post vaccination has been observed to loosely correlate with vaccine response, assays were carried out to investigate any association between production of sialylated IgG on day 7 and vaccine efficacy as measured by HAI titer by week 3 (Nakaya et al. (2011) Nature immunology 12, 786-795; and Wrammert et al. (2008) Nature 453, 667-671). Indeed, the abundance of sialylated glycoforms on anti-HA IgG produced by day 7 post vaccination was predictive of subsequent increase in HAI activity (FIG. 4a). In addition, sialylated glyco form abundance predicted affinity of anti-HA IgG at week 3 post vaccination (FIG. 4b). These data suggested that the abundance of sialylated Fc glycoforms produced during plasmablast expansion following TIV vaccination could regulate the quality of the overall vaccine response.

Figure 5A:
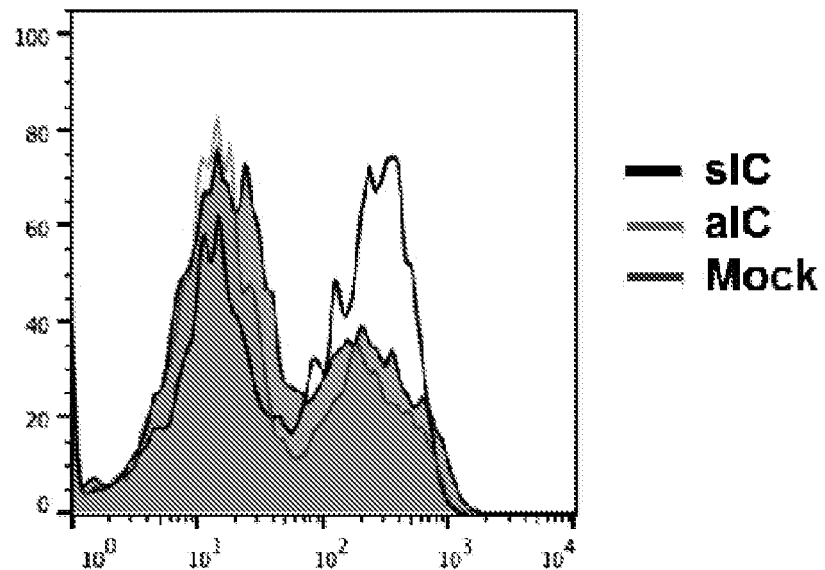
FIGS. 5A, 5B, 5C, and 5D are a set of diagrams showing sFc in ICs trigger upregulation of FcγRIIb on B cells. (A) sialylated ICs (sIC) or asialylated IC (aIC) were generated from pooled, post-vaccination human IgG and A/California/04/2009 HA protein, as described in Experimental Procedures. Human, CD19+ PBMCs were treated with IL-4 (200 ng/mL) and CD40L (5 ug/mL) for 20 h to increase surface expression of CD23 prior to incubation (24 h) with sIC, aIC or HA protein alone. FACS analysis of cells following incubation revealed increased FcγRIIB expression on cells incubated with sIC but not aIC or HA. (B) Similarly, sIC or aIC were generated from PY102, an anti-A/Puerto Rico/8/34 (PR8) mAb and PR8 HA protein. BJAB B cells were treated with IL-4 and CD40L as in (A), prior to incubation (6 hr) with sIC, aIC or HA protein alone (mock) at the indicated concentrations. As described above, incubation with sIC but not aIC or HA alone, induced increased FcγRIIB expression on B cells. (C) Antigen-specific peripheral B cells from mice primed with sIC showed increased expression of FcγRIIB, whereas mice primed with aICs or mock primed (NM) showed no elevation in peripheral B cell FcγRIIB expression. (D) Splenic B cells within the light and dark zones of the germinal center (GC) from mice primed with sIC showed increased expression of FcγRIIB, whereas mice primed with aICs or mock primed showed no elevation in GC B cell FcγRIIB expression. Increased FcγRIIB expression was not present in CD23 knockout mice (CD23−/−) primed with sIC.
Figure 5B:
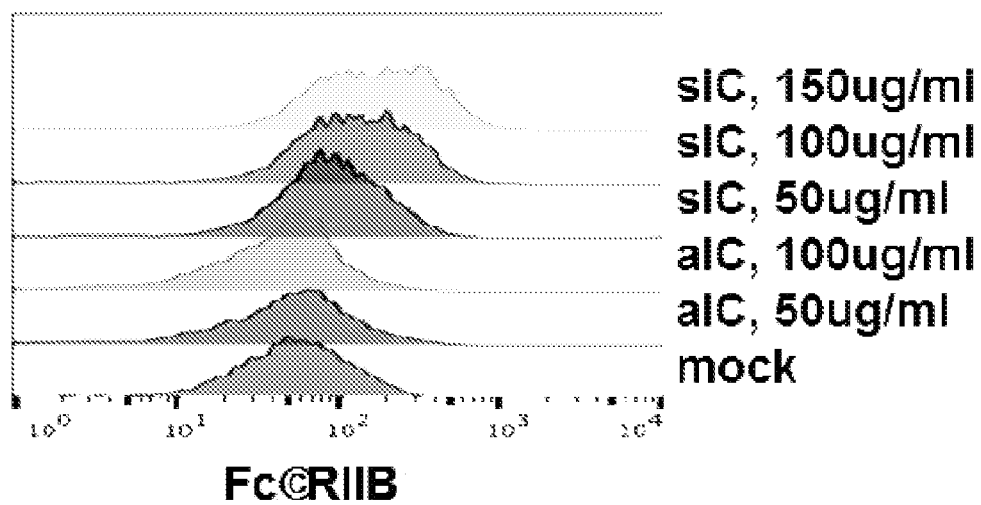
Figure 11:
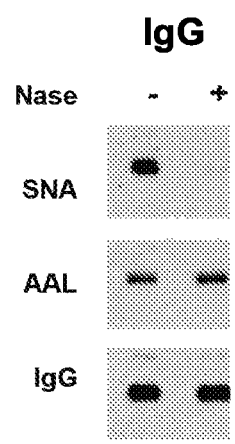
FIG. 11 shows neuraminidase treatment of polyclonal human IgG preparations. Representative western blot demonstrating removal of sialic acids from IgG by neuraminidase treatment. IgGs were probed with *Sambucus nigra* lectin (SNA), which binds preferentially to sialic acid attached to terminal galactose in α-2,6 or α-2,3 linkage, or with *Aleuria aurantia* lectin (AAL), which binds preferentially to fucose linked (α-1,6) to N-acetylglucosamine or to fucose linked (α-1,3) to N-acetyllactosamine related structures (control lectin), or with anti-Fc (IgG) to detect IgG protein. Neuraminidase treatment removed nearly all sialic acids detectable with SNA lectin from IgG preparations.

Example 5 Sialylated Fc Glycoforms in ICs Trigger Upregulation of FcγRIIb on B Cells, Resulting in Production of Higher Affinity IgGs To determine the mechanisms by which sFc within immune complexes might modulate B cell activation, assays were carried out to study the effects of sFc ICs on B cells in a variety of in vitro and in vivo assays. Pooled IgG from week 3 post-vaccination, either with native sialylated glycoform levels (17.6% on anti-HA IgG) or neuraminidase treated (asialylated) (FIG. 11) was complexed with California/04/2009 (Cal/09) H1 HA protein in an approximate molar ratio of 30:1 polyclonal IgG:HA trimer. These ICs were incubated with human CD19+ PBMCs and analysis after 24 hour incubation revealed increased expression of FcγRIIB, the inhibitory Type 1 Fc receptor, on cells incubated with the sialylated ICs (sIC), but not asialylated IC (aIC) or HA protein alone (FIG. 5a). Similarly, a recombinant anti-HA monoclonal antibody (mAb), PY102 (Dinca et al. (1993) Viral immunology 6, 75-84), was expressed with sialylated Fc glycoforms (23.7% sFc), or in an asialylated form, and was mixed with A/PR8/1934 H1 HA protein in molar ratio of 3:1 IgG:HA trimer to form sIC and aIC. These mAb IC were then incubated with BJAB cells and, consistent with the primary B cell assay, incubation with sICs, but not aIC or HA protein alone induced upregulation of FcγRIIB expression (FIG. 5b).

Figure 5C:
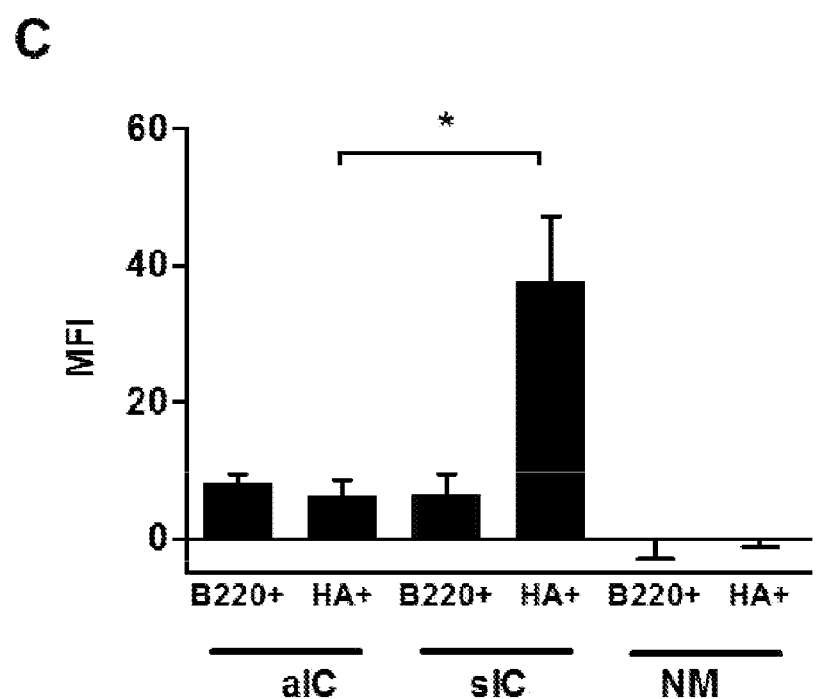
Figure 5D:
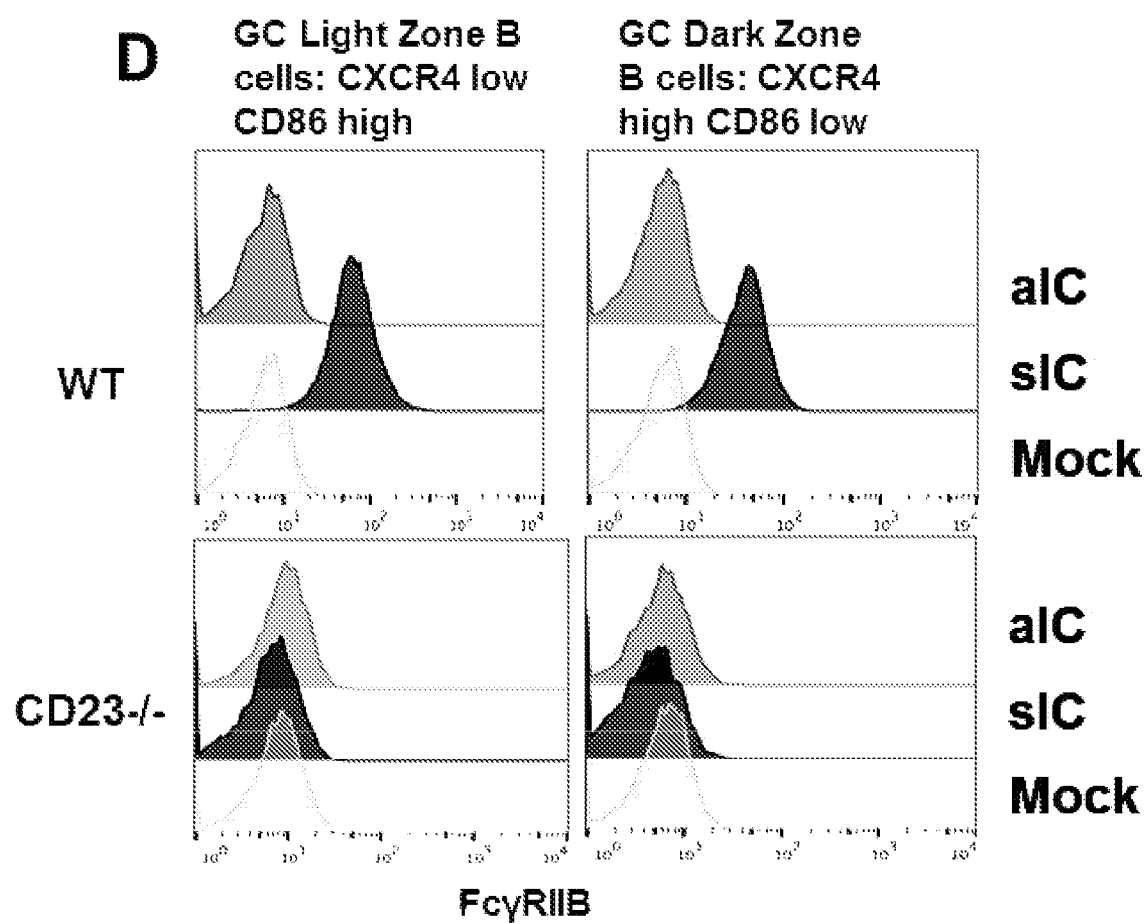

Next, to determine how sialylated ICs might affect B cells in vivo, the human post-vaccination IgG ICs (sIC and aIC) were used to prime mice, followed by HA protein boost in PBS 3 weeks later. Antigen-specific peripheral B cells from mice primed with sIC showed increased expression of FcγRIIB, whereas mice primed with aICs showed no elevation (FIG. 5c). Similarly, sIC or aIC made from mAb PY102 and HA protein were used to vaccinate mice; 3 days post vaccination, germinal center B cells (light zone and dark zone) from mice immunized with sICs, but not aICs or HA alone had increased FcγRIIB expression (FIG. 5d). Because CD23 is the only Type II FcR expressed on B cells, next assays were carried out to determine whether upregulation of FcγRIIB was dependent on CD23 expression. CD23 deficient mice did not display upregulation of FcγRIIB on germinal center B cells, demonstrating that sICs acted through CD23 to trigger upregulation of B cell FcγRIIB (FIG. 5d).

Example 6 IgG Elicited by Sialylated ICs are Higher Affinity for Antigen

Figures 6A, 6B, 6C, 6D:
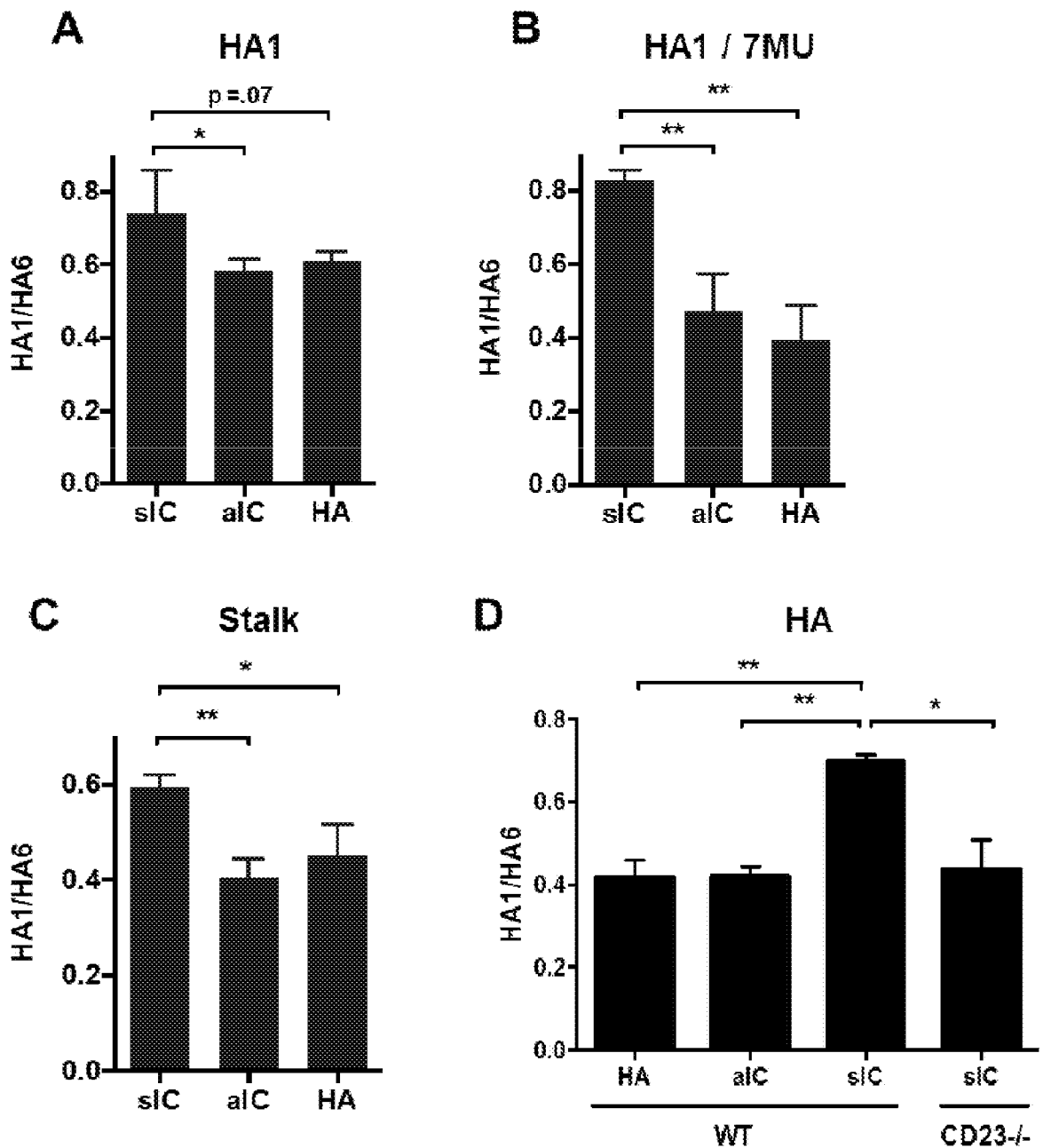
FIGS. 6A, 6B, 6C, 6D, and 6E are a set of diagrams showing sFc in ICs elicit higher affinity IgG. (A,B) IgGs elicited by human, polyclonal IgG sIC had significantly higher affinity for the globular head, (C) the stalk domain of the HA protein, (D) and the wild-type A/California/04/2009 H1 subtype HA protein when compared with the affinities of IgG elicited by aIC or HA alone. Only wild-type mice and not CD23 deficient mice generated higher affinity, anti-HA IgGs in response to an immunization protocol with sIC priming. Binding affinities were expressed as a ratio of IgG binding to low density/high density HA. Affinity measurement in (B) was determined by 7M urea ELISA, expressed IgG bound to HA following 7M urea treatment/IgG bound without 7M urea treatment. (E) SPR analysis of off-rate constant of polyclonal IgG elicited by mAb PY102-HA ICs in wild-type or CD23−/− mice. sIC priming protocol in wild-type mice elicited approximately 10-20 fold higher affinity IgGs over aIC priming or sIC priming in CD23−/− mice. $*p<0.05$; $p<0.01$; $*$ $p<0.001$: $****p<0.0001$ determined by two-tailed student's t test.
Figure 6E:
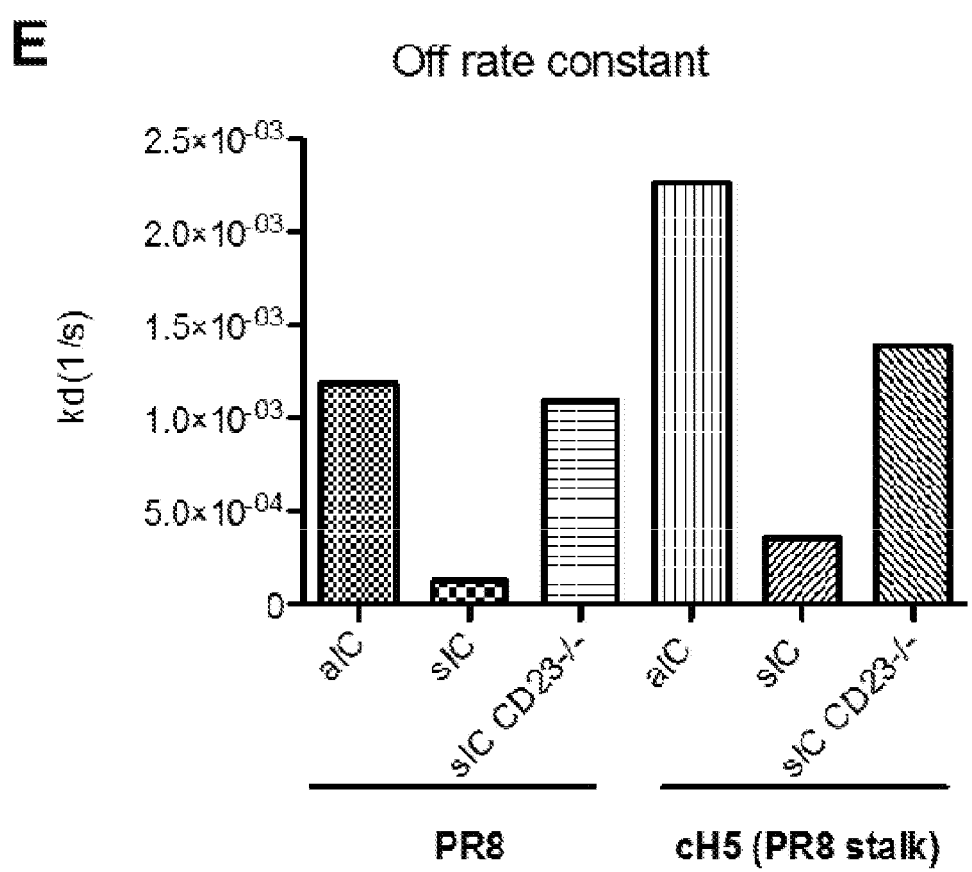

Increased FcγRIIB expression is known to elevate thresholds for selection of B cells based on affinity of BCR, thus, the affinity of anti-HA IgG elicited by immunization with sICs or aIC or by HA alone was characterized (Bolland et al. (2000) Immunity 13, 277-285; Moll et al. (2004) Journal of immunology 173, 4724-4728; and Pearse et al. (1999) Immunity 10, 753-760). The affinity of IgGs elicited by polyclonal human ICs was measured using an established affinity ELISA assay that was modified for evaluation of anti-HA IgGs that measures the ratio of high-affinity to all-affinity binding IgGs (Herzenberg et al. (1980) The Journal of experimental medicine 151, 1071-1087; Kaisho et al. (1997) Science 276, 412-415; and Roes et al. (1993) The Journal of experimental medicine 177, 45-55). The affinity for HA1 was also evaluated using a method that measures the quantity of IgG remaining bound following treatment with 7M urea. IgGs elicited by the sIC priming protocol had significantly higher affinity for HA1 (primarily globular head), the highly conserved stalk domain of the HA protein, and for the complete HA glycoprotein (FIG. 6a,b,c,d). Consistent with the lack of FcγRIIB upregulation using the sIC priming protocol in CD23 deficient mice (FIG. 5d), elevated affinity of elicited IgGs was not achieved in CD23 deficient mice (FIG. 6d). The affinity of polyclonal IgGs elicited by mAb PY102-HA ICs for the PR8 H1 protein or the PR8 stalk domain was assessed using surface plasmon resonance (SPR) analysis. The polyclonal serum antibody dissociation off-rate for anti-HA IgG from mice primed with sIC was found to be approximately 10-20 fold lower than that of IgG from mice primed with aIC or CD23 deficient mice that received sIC (FIG. 6e).

Figures 7A, 7B:
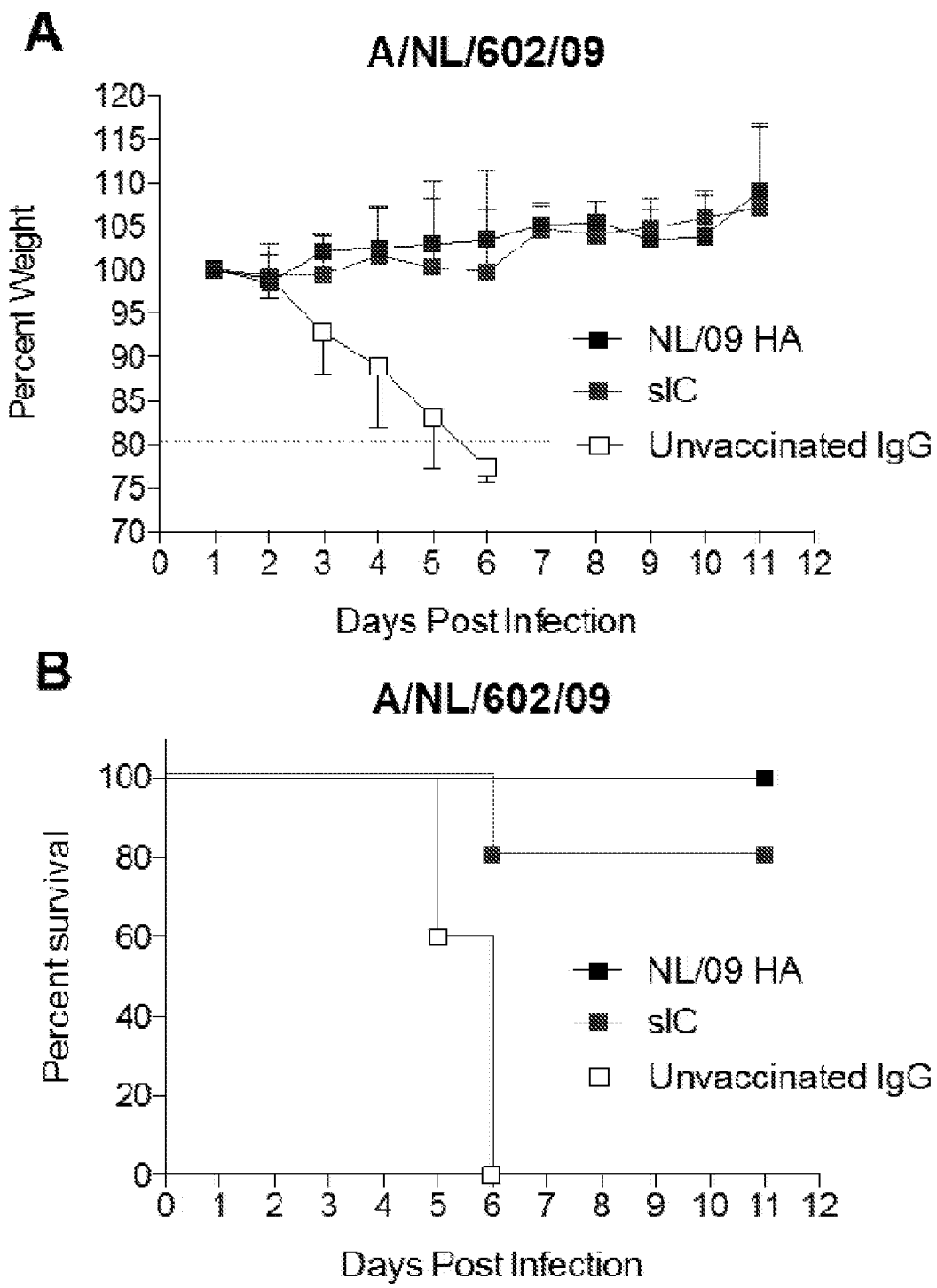
FIGS. 7A, 7B, 7C, 7D, 7E, 7F, 7G, 7H, 7I- and 7J are diagrams showing immunization with sIC elicit IgGs with greater breadth of protective potency against distinct influenza viruses. (A,B) Purified IgGs were pooled from mice primed with polyclonal human sIC (Cal/09 HA) or Cal/09 HA alone followed by two boost immunizations of Cal/09 HA in IFA/CFA. IgG from either pool conferred equivalent protection against A/Netherlands/602/2009 (H1N1). (C,D) In contrast, only IgGs elicited by priming with sICs conferred anti-stalk-mediated protection against the chimeric cH5/1 virus that expresses a hemagglutinin with an H1 stalk domain and an irrelevant H5 subtype globular head. (E,F) Purified IgGs were pooled from mice primed with monoclonal PY102-PR8 HA ICs or PR8 HA alone. ICs used were: sIC in wild-type mice, sIC in CD23−/− mice or aIC. IgG from either pool conferred equivalent protection against A/PR8/1934 virus (H1N1). (G,H) In contrast, only IgG elicited by sIC protected mice from challenge with either A/FM/1/1947 (H1N1) virus or (I,J) A/Netherlands/602/2009 virus (FIG. 7g-j). The number of animals used was 5-10 per group in each experiment.
Figure 7C:
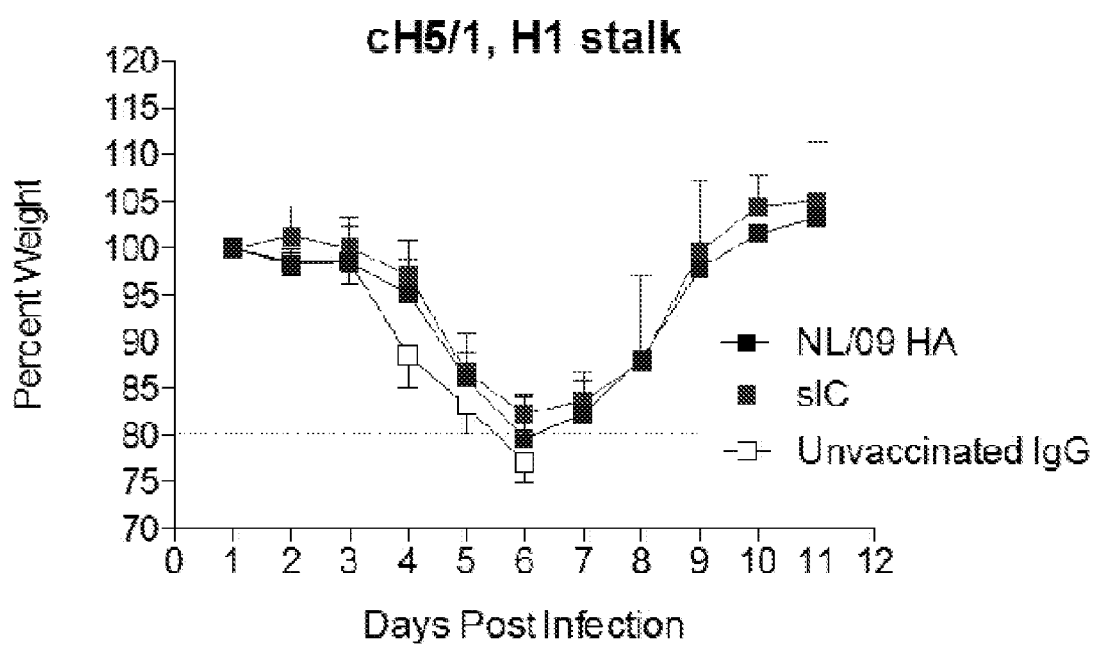
Figure 7D:
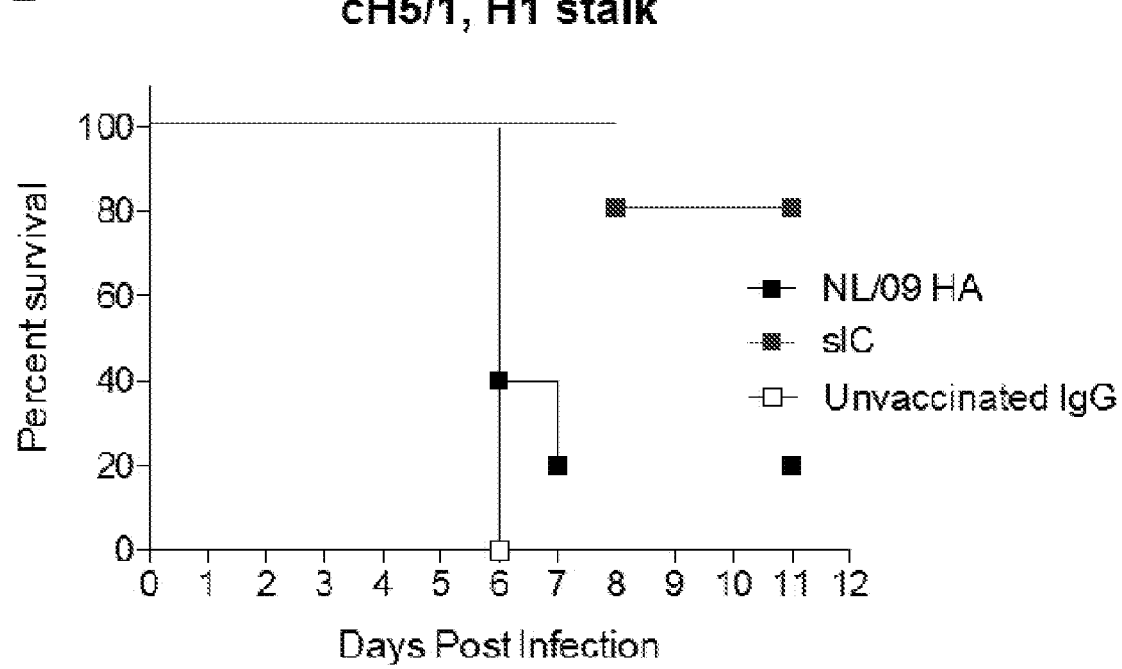
Figure 12A:
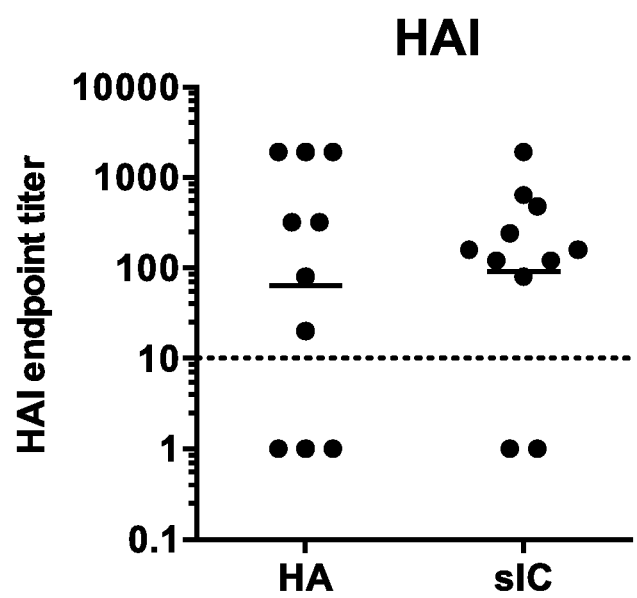
FIGS. 12A. 12B, 12C, 12D, 12E, 12F, and 12G are diagrams showing characterization of IgG elicited by sIC or HA. (A) HA or sIC priming elicited equivalent HAI titers against virus expressing the homologous HA used in vaccination (Netherlands/602/2009, H1N1). (B,C) Binding titer to Cal/09 protein or to the H1 stalk domain were equivalent in IgG pools elicited by HA or sIC. 1:500 dilution shown was in linear range for both preparations. (D,E) Endpoint binding titer to Cal/09 protein or to the H1 stalk domain in mice immunized with the sIC or HA priming protocol (described in methods). (F,G) Binding curves of purified IgG used in mouse challenge experiments to Cal/09 HA protein or to the cH5/1 H1 stalk domain protein.
Figure 12B:
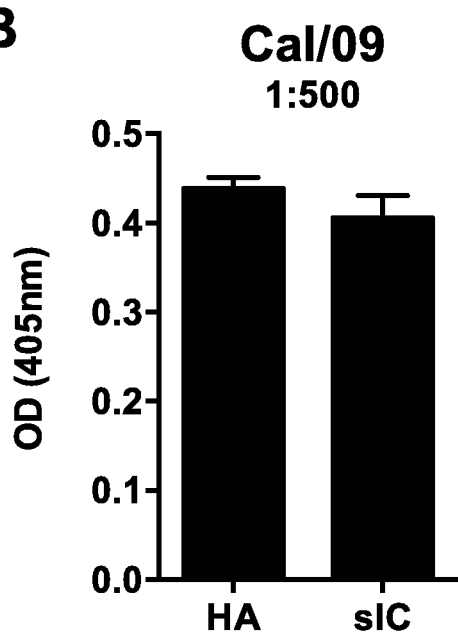
Figure 12C:
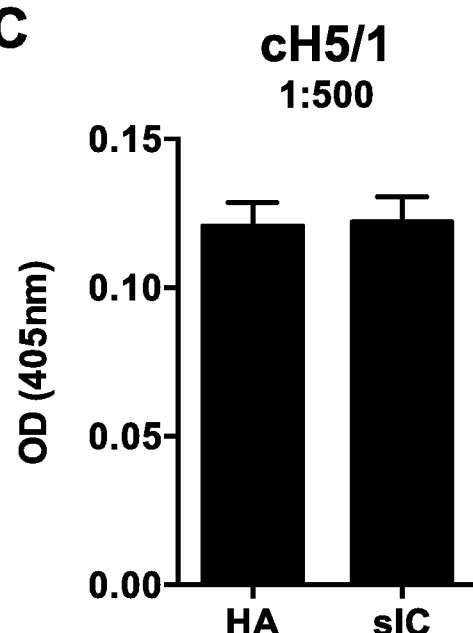
Figures 12D, 12E, 12F, 12G:
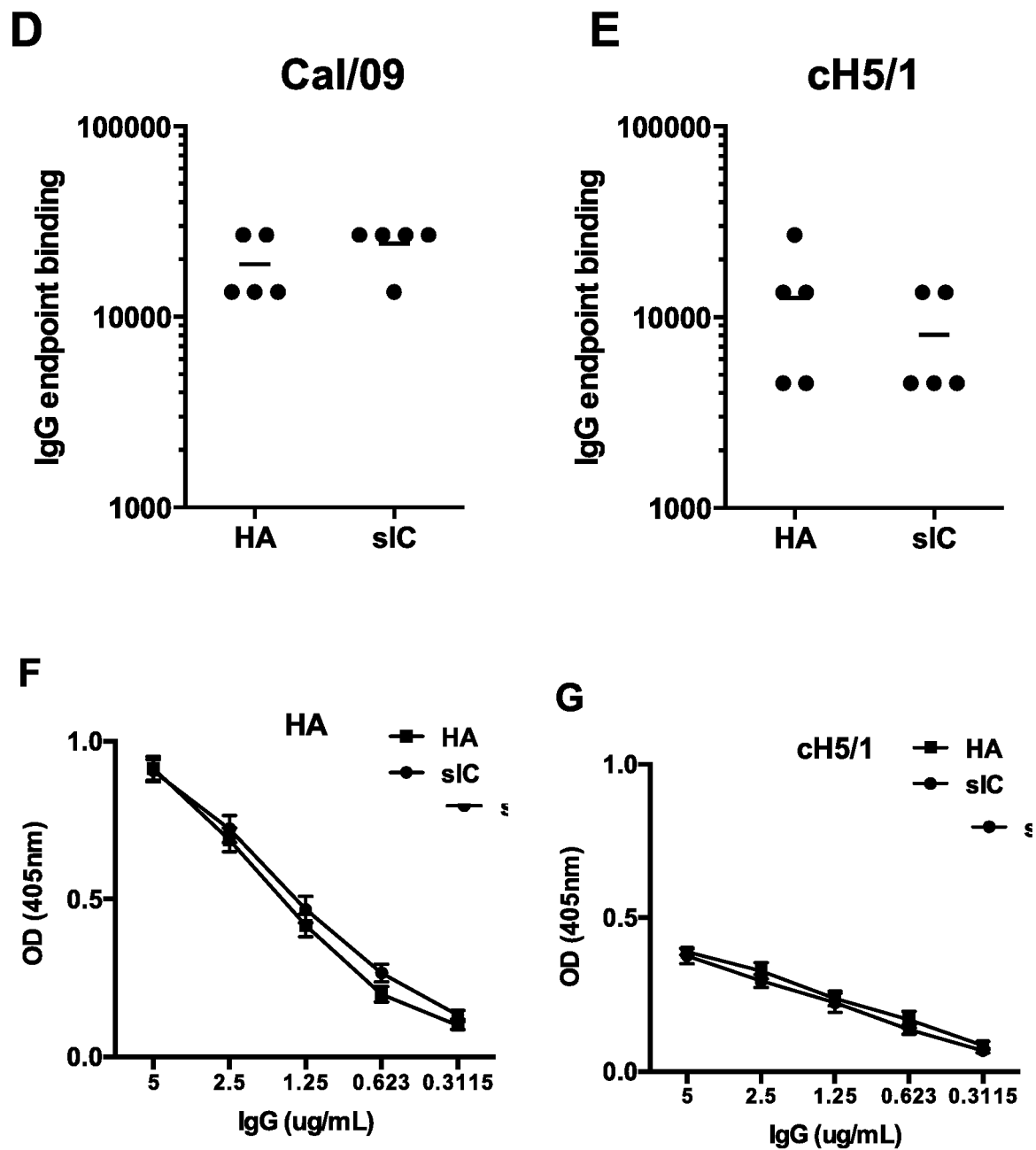

Example 7 Higher Affinity IgGs Mediate HA Stalk-Based Protection Against Lethal Influenza Virus Challenge To determine any functional significance of increasing affinity of anti-HA IgGs, assays were carried out to test pooled IgG from mice primed with sIC or HA alone for protective activity (pools were derived from sera tested in FIG. 6). IgG pools had equivalent HAI endpoint titers using virus expressing the homologous HA used for vaccination (A/Netherlands/602/2009) (FIG. 12a) and equivalent binding activity for Cal/09 or Cal/09 stalk proteins (FIG. 12b, c,d,e). For challenge experiments, virus was pre-incubated with purified IgG prior to intranasal infection; thus, weight loss was a function of dose of infectious virus remaining after incubation with IgG pools. On challenge, equivalent protection was observed against the H1N1 virus A/Netherlands/602/2009 (FIG. 7a,b). In contrast, when evaluated only anti-stalk IgGs for protective activity using a virus that expresses a chimeric hemagglutinin molecule (cH5/1) comprised of the highly conserved H1 stalk domain and an irrelevant head subtype domain (H5), a difference in protective potency of the IgG pools was observed. Only the higher affinity IgGs elicited by priming with sIC conferred anti-stalk-mediated protection (FIGS. 7c and d).

Figure 7E:
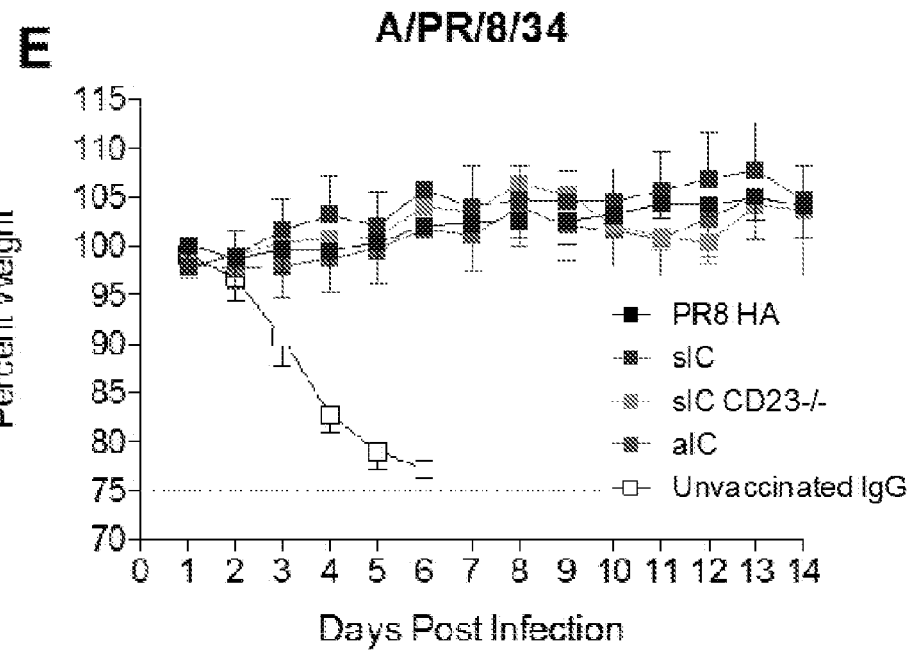
Figure 7F:
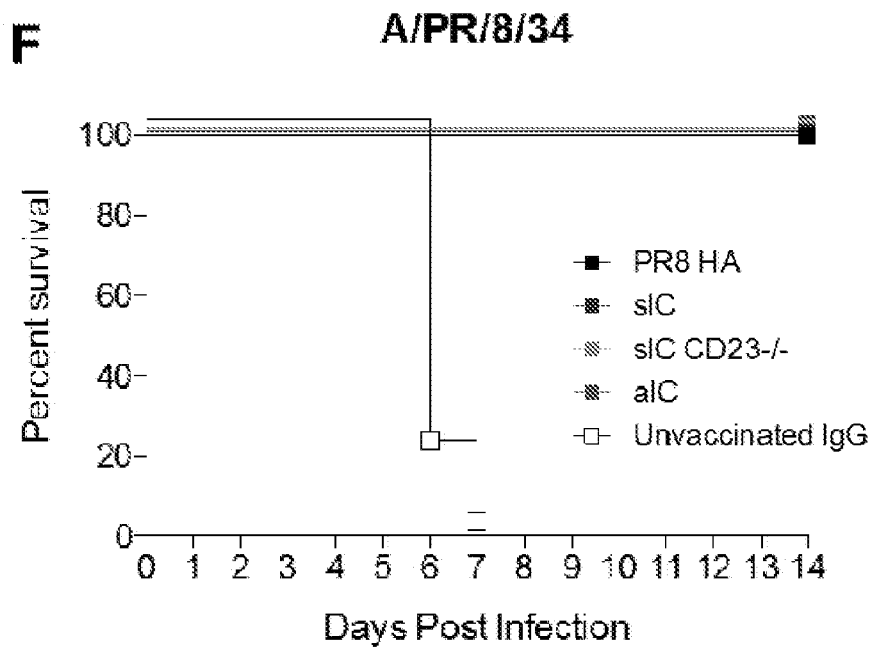
Figure 7G:
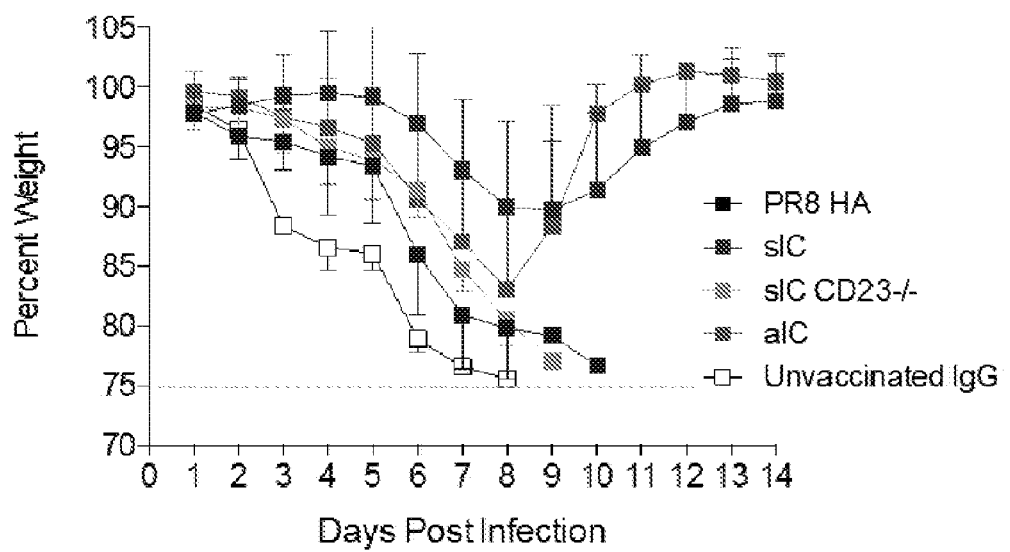
Figure 7H:
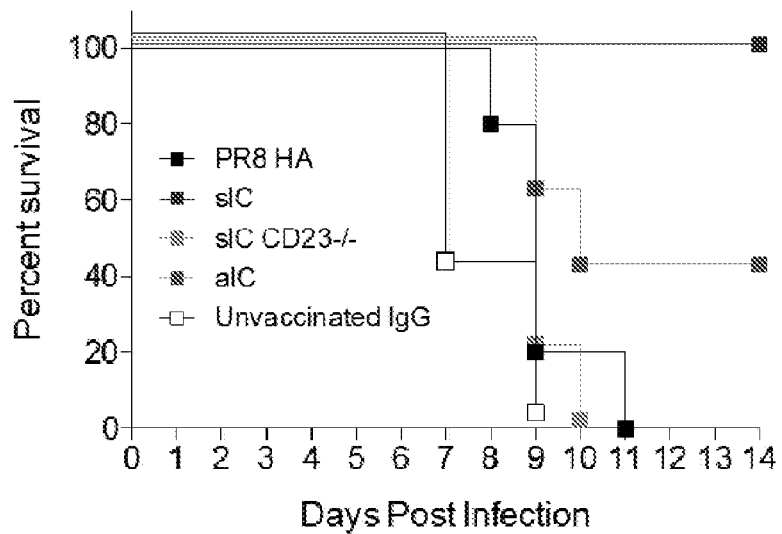
Figure 7I:
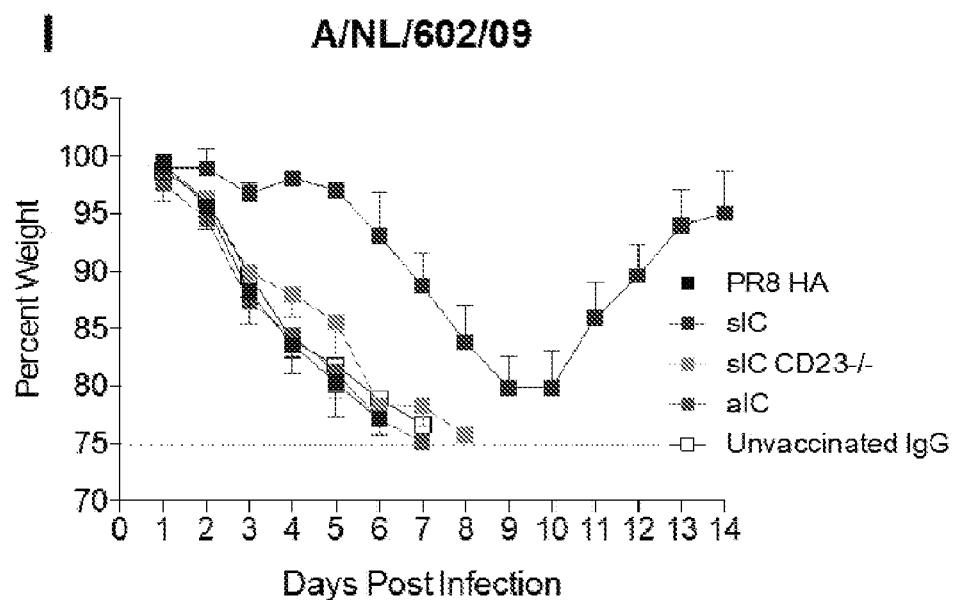
Figure 7J:
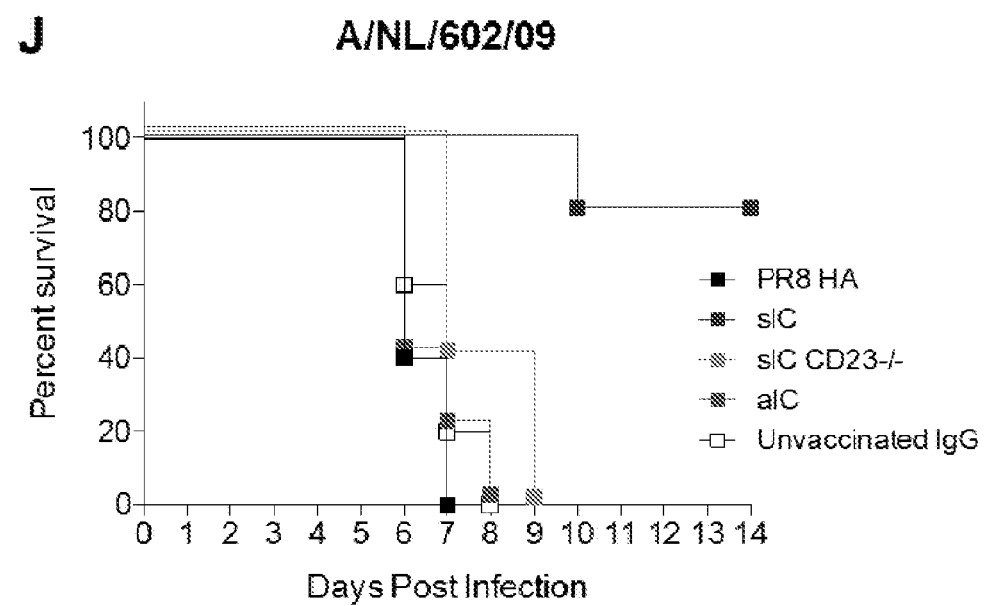

Next, equivalent challenge experiments were performed using IgG from mice immunized with mAb PY102+PR8 H1 HA IC (sIC in wild-type mice, sIC in CD23-deficient mice or aIC) or PR8 HA alone. Mice were challenged with virus expressing the homologous H1 HA used for vaccination (A/PR8/1934, H1N1) and, as before, complete protection was achieved with all IgG pools (FIGS. 7e and f). In contrast, only IgG elicited by sIC protected mice from challenge with either A/FM/1/1947 H1N1 virus or A/Netherlands/602/2009 H1N1 virus (FIGS. 7g-j).

Example 8 IC of Human Anti-TIV IgG and TIV Enhanced Various Aspects of IgG Response Mice were subjected to primary immunization at Day 0 (DO) and received the 2014-15 Fluvirin Trivalent inactivated influenza vaccine (TIV) at a dosage of 15 ug HA per mouse (5 ug each HA). The TIV contained an A/California/7/2009 (H1N1)pdm09-like virus, an A/Texas/50/2012 (H3N2)-like virus; and a B/Massachusetts/2/2012-like virus. The TIV was given alone, or in combination with human anti-TIV IgG (human hyperimmune IgG) taken 3 weeks post TIV administration. The hyperimmune IgG was treated with neuraminidase to remove sialic acids (asialylated IgG or aIgG) or left in native state (sialylated IgG or sIgG)). The untreated IgG had 27% sFc on anti-HA IgG, measured by mass spectrometry. Each of the mice then received a boost immunization at day 14 (D14) of a composition having the TIV (15 ug total HA) and an MF59 adjuvant. Finally, the mice were bled on day 24 (D24) and IgG was purified from serum by protein G purification for further analysis.

First, effects of the ICs on the breadth of IgG response were examined. The results were shown in FIG. 15. It was found that breadth of the anti-HA response was enhanced by the TIV+sIgG (sIC) administration over TIV alone or TIV+aIgG (aIC). Binding to homologous antigen (TIV) or the homologous H1 HA component (Cal09 H1) was not significantly different between groups. Binding to a heterologous H1 (Bris07 H1) or heterosubtypic H3 (Bris07 H3) or H5 (Hunan02 H5) was enhanced by administration of sIC over aIC or TIV alone.

Figure 16:
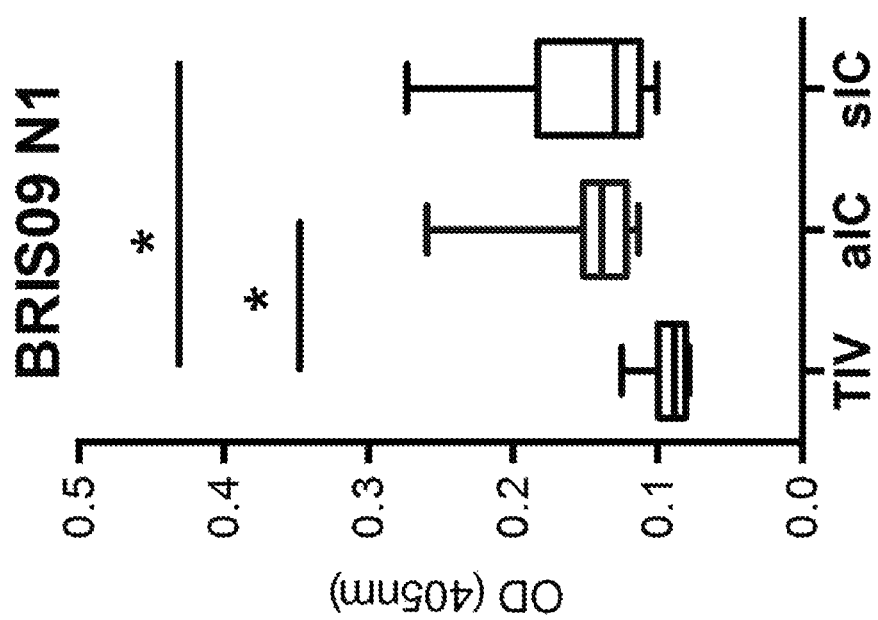
FIG. 16 is a diagram showing that polyclonal TIV sIC or aIC enhanced anti-N1 IgG response.

Second, effects of the ICs on the anti-N1 IgG response were examined. The results were shown in FIG. 16. It was found that administration of either TIV+sIgG (sIC) or TIV+aIgG (aIC) enhanced binding to the N1 subtype neuraminidase protein. While the sIC enhanced the IgG response primarily through Type 2 Fc receptor signaling, the aIC modulated the response through Type 1 Fc receptor interactions. The Fluvirin TIV vaccine (and other TIV vaccine preparations) contained mostly hemagglutinin proteins, but also contain neuraminidase proteins—Fluvirin contains 5 ug N1 protein per dose (MBio. 2015 Mar. 10; 6(2):e02556. doi: 10.1128/mBio.02556-14.).

Figure 17:
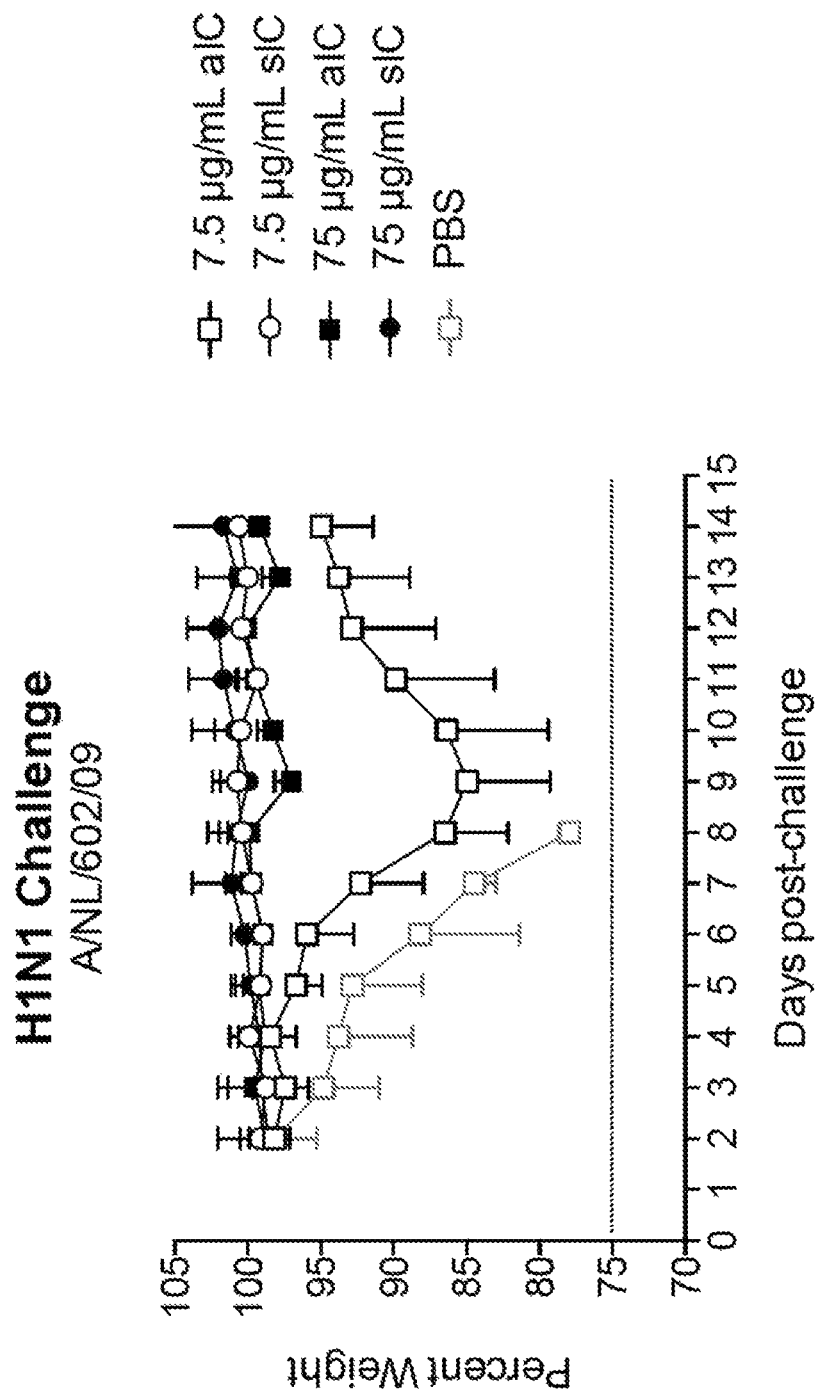
FIG. 17 is a diagram showing that immunization with TIV sICs enhanced potency of IgG response.

Third, effects of the ICs on the potency of IgG response were examined. Briefly, purified IgG from mice vaccinated as previously described with TIV sIC or aIC was transferred to naïve mice 1 hour prior to challenge with 10 mLD$_{50}$ A/Netherlands/602/2009 virus (H1N1). IgG was transferred in 100 ug PBS by intraperitoneal administration at either 75 ug/mL or 7.5 ug/mL. The results were shown in FIG. 17. All mice that received 75 ug/mL IgG were protected from weight loss following challenge, but at the 7.5 ug/mL dose, only those receiving sIC-elicited IgG were protected. The results indicate that potency of protective IgG was enhanced by TIV+sIgG (sIC) administration.

Figures 18A, 18B:
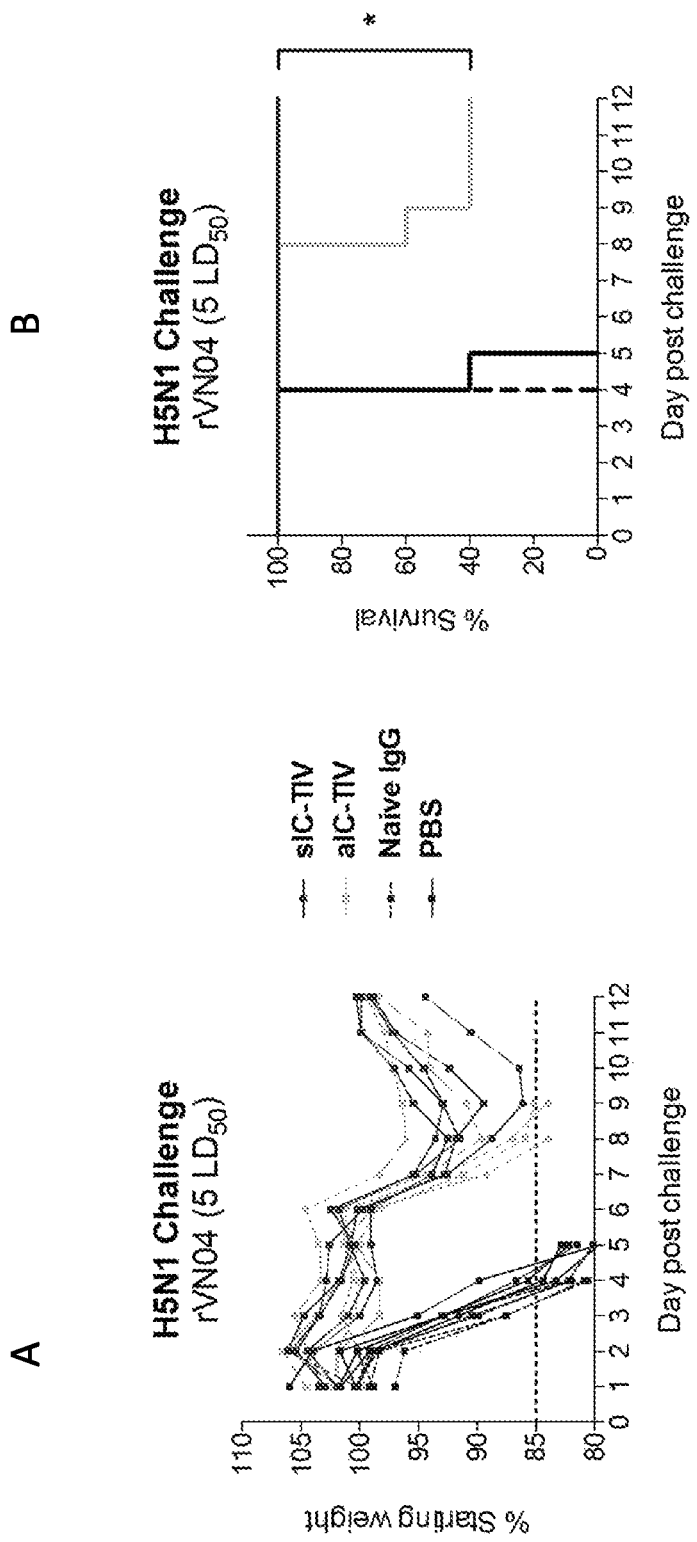
FIGS. 18A and 18B are diagrams showing that immunization with TIV sICs increased protection against H5N1 challenge: (A) changes in body weights; and (B) survival rates.
Figure 19:
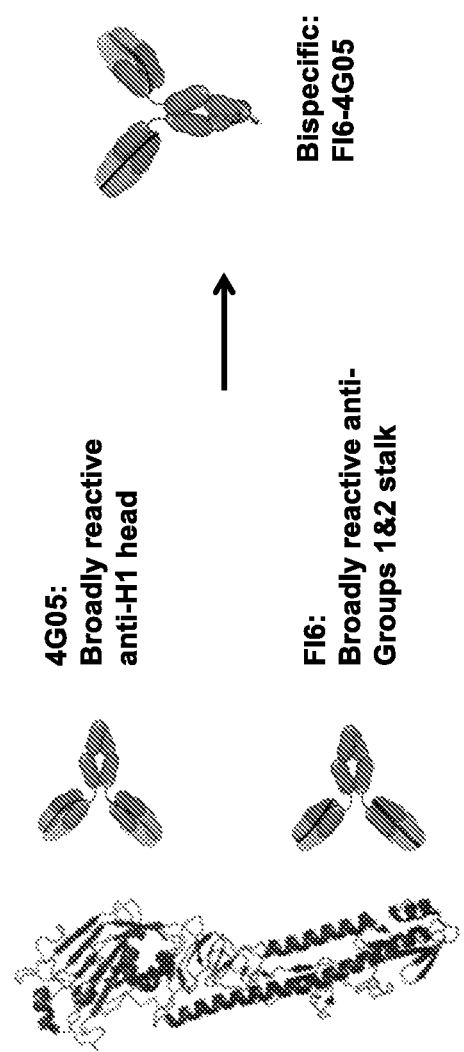
FIG. 19 is a diagram showing an sFc bispecific FI6-4G05 monoclonal antibody (mAb).

Finally, protection against H5N1 challenge was examined in the mice. Briefly, purified IgG from mice vaccinated as previously described with TIV sIC or aIC was transferred to naïve mice 1 hour prior to challenge with 10 mLD$_{50}$ HALo virus (H5N1). IgG was transferred in 100 ug PBS by intraperitoneal administration at 75 ug/mL. The Influenza A/Vietnam/1203/04 H5N1 HALo mutant was an attenuated H5N1 virus generated from wild-type Influenza A/Vietnam/1203/04 (H5N1) virus by reverse genetics, as described in Steel, J., et al. J Virol. 2009 February; 83(4):1742-53). The results were shown in FIG. 18. It was found that breadth of protective IgG was enhanced by TIV+sIgG (sIC) administration. The results indicate that immunization with TIV sICs increased protection against H5N1 challenge.

Example 9 Bispecific IC Enhanced Various Aspects of IgG Response

In this example, an IC vaccine having TIV or H1/H3 protein and a bispecific, broadly reactive anti-HA monoclonal antibody was examined.

The bispecific monoclonal antibody, F16/19-4G05, had broad reactivity against different HA proteins and was generated in the manner as described in Nat Biotechnol. 1998 July; 16(7):677-81. To make this bispecific monoclonal antibody, a set of heavy and light chains from mAb 19-4G05 (Proc Natl Acad Sci USA. 2012 Jun. 5; 109(23): 9047-52) was combined with that from mAb F16 (Science 333:850-856.). The mAb 19-4G05 antibody is a broadly reactive anti-H1 head antibody while the mAb F16 antibody is a broadly reactive anti-Groups 1&2 stalk antibody. The sFc bispecific F16/19-4G05 monoclonal antibody was expressed in the manner described in Cell. 2015 Jul. 2; 162(1):160-9. About 23% of the F16/19-4G05 monoclonal antibody was sialylated.

Frist, an IC vaccine having TIV and the bispecific, broadly reactive anti-HA monoclonal antibody was examined. To that end, mice were immunized with TIV. Briefly, TIV was administered alone or with the F16/19-4G05 bispecific monoclonal antibody. Two weeks later, the mice were boosted with TIV and a ribi adjuvant. Two weeks post boost, the mice were bled for analysis of serum IgG.

Effects of the ICs on the breadth of IgG response were examined. The results were shown in FIG. 20. It was found that the breadth of the anti-HA response was enhanced by TIV+sFc bimAb (TIV+bimAb) administration over TIV alone. Binding to homologous H1 HA (Cal09 H1) was enhanced, as was binding to heterologous H1 (Bris07 H1) or heterosubtypic H3 (Bris07 H3) or H5 (VN/04 H5) HA proteins over IgG elicited by TIV alone.

Second, an IC vaccine having H1/H3 protein and the bispecific monoclonal antibody was examined. Similarly, to immunize mice, pure H1 and H3 proteins (5 ug/HA) were administered alone or with the sFc F16/19-4G05 bimAb. Two weeks later, the mice were boosted with H1 and H3 proteins (5 ug/HA) in an alum adjuvant. Two weeks post boost, the mice were bled for analysis of serum IgG. Affinity ELISA was carried out in the manner described in Cell. 2015 Jul. 2; 162(1):160-9. The results were shown in FIG. 21.

It was found that affinity of the anti-HA response was enhanced by administration of H1 and H3 proteins with the sFc F16/19-4G05 bimAb (HA+sFc bimAb) over administration of H1 and H3 proteins alone (HA alone). Affinity for homologous H1 HA (PR8 H1) was enhanced, as was the affinity for the PR8 stalk domain (H1 stalk) and the A/Hong Kong/1968 stalk domain (H3 stalk).

It was also found that immunization with H1+H3 proteins with the sFc bimAb also enhanced breadth of IgG response. As shown in FIG. 22, the breadth of the anti-HA response was enhanced by administration of H1 and H3 proteins with the sFc F16/19-4G05 bimAb (4G05/FI6 sIC) over administration of H1+H3 proteins alone (HA alone). Binding to the 2014-15 TIV preparation containing a heterologous H1 HA (A/California/7/2009-like virus) and heterologous H3 HA (A/Texas/50/2012-like virus) was enhanced, as was binding to other heterologous H1 (Bris07 H1), H3 (Bris07 H3) and H5 (VN/04 H5) HA proteins over IgG elicited by administration of H1+H3 proteins alone (HA alone).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated immune complex comprising an antigenic agent and a protein, wherein the protein comprises an IgG Fc region and is capable of binding to a Type II Fc receptor, wherein the protein is at least 70% identical to SEQ ID NO: 1 and has a F to A mutation (F241A mutation) at a position corresponding to F241 of SEQ ID NO: 1, and wherein the immune complex is formulated for administering to a subject.

2. The immune complex of claim 1, wherein the protein comprises a sialylated form of the IgG Fc region.

3. The immune complex of claim 1, wherein the protein comprises an asialylated form of the IgG Fc region.

4. The immune complex of claim 3, wherein the protein is at least 80% identical to SEQ ID NO: 1.

5. The immune complex of claim 1, wherein the isolated protein specifically binds to the antigenic agent or conjugated to the antigenic agent.

6. The immune complex of claim 5, wherein the protein is an antibody or an Fc region-containing fragment thereof.

7. The immune complex of claim 1, wherein the antigenic agent comprises a polypeptide.

8. The immune complex of claim 7, wherein the polypeptide comprises the sequence of an antigen of a virus.

9. The immune complex of claim 8, wherein the virus is selected from the group consisting of a picoranovirus, a togovirus, a coronavirus, an arenavirus, a bunyavirus, a rhabdovirus, an orthomyxovirus, a paramyxovirus, a reovirus, a parvovirus, a papovovirus, an adenovirus, a herpesvirus, a varicella-zoster virus, and an RNA tumor virus.

10. The immune complex of claim 9, wherein the virus is selected from the group consisting of an influenza virus, a norovirus, a rotavirus, an Ebola virus, and a HIV.

11. The immune complex of claim 10, wherein the virus is an influenza virus.

12. The immune complex of claim 11, wherein the polypeptide comprises a stalk domain of the influenza virus.

13. The immune complex of claim 1, wherein the antigenic agent comprises a tumor antigen.

14. The immune complex of claim 6, wherein the antibody is a bi-specific antibody that binds (i) to two different epitopes of said antigenic agent or (ii) to said antigenic agent and a second antigenic agent respectively.

15. A pharmaceutical composition comprising an immune complex of claim 1 and pharmaceutically acceptable carrier.

16. A method of preventing a viral infection comprising administering to a subject in need thereof a therapeutically effective amount of an immune complex of claim 8.

17. A method of preventing a viral infection comprising administering to a subject in need thereof a combination of a therapeutically effective amount of an antiviral vaccine and an immune complex of claim 8.

18. A method of preventing an occurrence of a tumor, comprising administering to a subject the immune complex of claim 13.

19. A method of preventing tumor formation or enhancing survival of a subject having a tumor, the method comprising administering to a subject in need thereof an effective amount of the immune complex of claim 13.

20. The method of claim 19, further comprising administering to the subject an effective amount of at least one chemotherapeutic agent selected from the group consisting of 5-fluorouracil, cytarabine, oxaliplatin, paclitaxel and combinations thereof; thereby treating the tumor or enhancing survival of the subject having the tumor.

21. The method of claim 18, wherein the tumor is selected from the group consisting of colorectal carcinoma; lung carcinoma; breast carcinoma; melanoma; ovarian carcinoma; cervical carcinoma, pancreatic cancer; multiple myeloma; renal cell carcinoma; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL), and chronic lymphocytic leukemia (CLL).

* * * * *